United States Patent
Asanuma et al.

(10) Patent No.: US 12,288,329 B2
(45) Date of Patent: Apr. 29, 2025

(54) OPHTHALMIC APPARATUS, METHOD OF CONTROLLING THE SAME, AND RECORDING MEDIUM

(71) Applicant: Topcon Corporation, Tokyo (JP)

(72) Inventors: Kazunori Asanuma, Tokyo (JP); Yusuke Ono, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 386 days.

(21) Appl. No.: 17/800,536

(22) PCT Filed: Jan. 27, 2021

(86) PCT No.: PCT/JP2021/002714
§ 371 (c)(1),
(2) Date: Aug. 18, 2022

(87) PCT Pub. No.: WO2021/176893
PCT Pub. Date: Sep. 10, 2021

(65) Prior Publication Data
US 2023/0115056 A1    Apr. 13, 2023

(30) Foreign Application Priority Data

Mar. 5, 2020   (JP) ................................. 2020-037418

(51) Int. Cl.
*G06T 7/00*      (2017.01)
*G06T 5/00*      (2024.01)
(Continued)

(52) U.S. Cl.
CPC .............. *G06T 7/0012* (2013.01); *G06T 5/80* (2024.01); *G06T 7/13* (2017.01); *G06V 10/25* (2022.01);
(Continued)

(58) Field of Classification Search
CPC ........... G06T 7/0012; G06T 7/13; G06T 5/80; G06T 2207/10101; G06T 2207/30041; G06V 10/25; G06V 40/193
See application file for complete search history.

(56) References Cited

U.S. PATENT DOCUMENTS 9,265,411 B2 *  2/2016  Chen ..................... A61B 3/0025
9,372,067 B2 *  6/2016  Straub ................ G01B 9/02077
(Continued)

FOREIGN PATENT DOCUMENTS

JP     2011-147611 A     8/2011
JP     2012-75640 A      4/2012
(Continued)

OTHER PUBLICATIONS

International Search Report and Written Opinion mailed on Apr. 20, 2021, received for PCT Application PCT/JP2021/002714, filed on Jan. 27, 2021, 14 pages including English Translation.
(Continued)

*Primary Examiner* — Gregory M Desire
(74) *Attorney, Agent, or Firm* — XSENSUS LLP

(57) ABSTRACT

An ophthalmic apparatus of an aspect example includes an image acquiring unit, a first image region identifying processor, and a second image region identifying processor. The image acquiring unit is configured to acquire an anterior segment image constructed based on data collected from an anterior segment of a subject's eye by OCT scanning. The first image region identifying processor is configured to identify a first image region corresponding to a predetermined part of the anterior segment by analyzing a first part of the anterior segment image acquired by the image acquiring unit. The second image region identifying processor is configured to identify a second image region corresponding to the predetermined part based on the first image region identified by the first image region identifying processor, the
(Continued)

second image region being inside a second part that includes the first part as a proper subset.

28 Claims, 17 Drawing Sheets

(51) Int. Cl.
*G06T 5/80* (2024.01)
*G06T 7/13* (2017.01)
*G06V 10/25* (2022.01)
*G06V 40/18* (2022.01)

(52) U.S. Cl.
CPC .. *G06V 40/193* (2022.01); *G06T 2207/10101* (2013.01); *G06T 2207/30041* (2013.01)

(56) References Cited

U.S. PATENT DOCUMENTS

| | | | |
|---|---|---|---|
| 9,492,079 B2 * | 11/2016 | Walsh | A61B 3/113 |
| 9,560,963 B2 * | 2/2017 | Buckland | A61B 3/102 |
| 9,833,136 B2 * | 12/2017 | Bagherinia | G06T 7/0012 |
| 10,117,568 B2 * | 11/2018 | Reisman | A61B 3/102 |
| 10,660,519 B2 * | 5/2020 | Carrasco-Zevallos | A61B 3/1225 |
| 10,799,111 B2 * | 10/2020 | Schmoll | A61B 3/152 |
| 10,827,921 B2 * | 11/2020 | Ren | G06V 40/18 |
| 2005/0084179 A1 | 4/2005 | Hanna et al. | |
| 2012/0083667 A1 | 4/2012 | Isogai et al. | |
| 2012/0140174 A1 | 6/2012 | Hee et al. | |
| 2013/0188140 A1 | 7/2013 | Bagherinia et al. | |
| 2013/0258280 A1 | 10/2013 | Goto | |
| 2013/0258283 A1 | 10/2013 | Goto et al. | |
| 2013/0301008 A1 | 11/2013 | Srivastava et al. | |
| 2014/0211158 A1 | 7/2014 | Oyaizu et al. | |
| 2015/0085252 A1 | 3/2015 | Fujimura et al. | |
| 2015/0245765 A1 | 9/2015 | Fujii et al. | |
| 2015/0327762 A1 | 11/2015 | Isogai et al. | |
| 2016/0038021 A1 | 2/2016 | Bagherinia et al. | |
| 2016/0317029 A1 | 11/2016 | Srivastava et al. | |
| 2016/0345822 A1 | 12/2016 | Fujimura et al. | |
| 2016/0360962 A1 | 12/2016 | Okamoto et al. | |
| 2019/0076012 A1 | 3/2019 | Kobayashi | |
| 2019/0099074 A1 | 4/2019 | Murata | |
| 2019/0156100 A1 | 5/2019 | Rougeaux et al. | |
| 2020/0035362 A1 | 1/2020 | Abou Shousha et al. | |
| 2021/0161376 A1 | 6/2021 | Ono | |

FOREIGN PATENT DOCUMENTS

| | | |
|---|---|---|
| JP | 2013-226383 A | 11/2013 |
| JP | 2013-248376 A | 12/2013 |
| JP | 2014-500096 A | 1/2014 |
| JP | 2015-504740 A | 2/2015 |
| JP | 2015-515894 A | 6/2015 |
| JP | 2015-160103 A | 9/2015 |
| JP | 2017-158728 A | 9/2017 |
| JP | 2017-169671 A | 9/2017 |
| JP | 2019-63242 A | 4/2019 |
| JP | 2019-88382 A | 6/2019 |
| JP | 2019-519859 A | 7/2019 |
| JP | 2019-213740 A | 12/2019 |

OTHER PUBLICATIONS

Extended European Search Report issued Feb. 23, 2024, in corresponding European Patent Application No. 21764776.7, 8pp.
Office Action issued on Apr. 9, 2024, in corresponding Japanese patent Application No. 2020-037418, 20 pages.
Dimitrios Ioannou et al., "Circle recognition through a 2D Hough Transform and radius histogramming", Image and Vision Computing, vol. 17, 1999, pp. 15-26, total 12 pages.

* cited by examiner

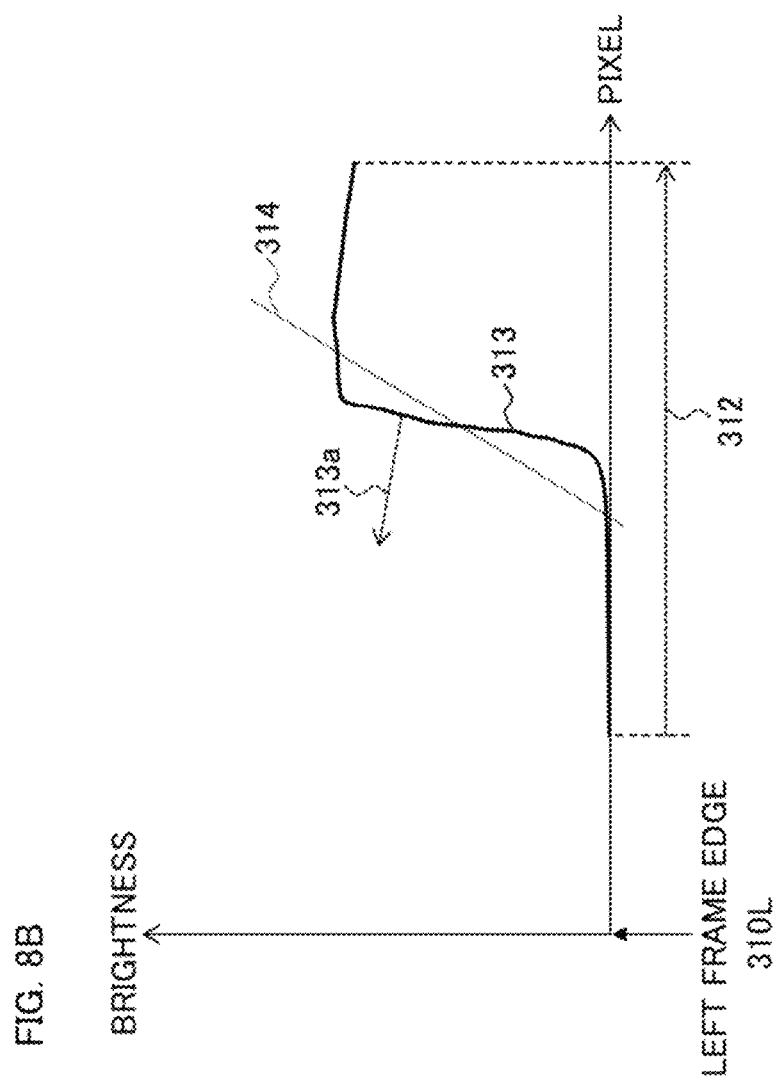

OPHTHALMIC APPARATUS, METHOD OF CONTROLLING THE SAME, AND RECORDING MEDIUM

CROSS-REFERENCE TO RELATED APPLICATIONS

This application is a national stage (under 35 U.S.C. 371) of International Patent Application No. PCT/JP2021/002714, filed Jan. 27, 2021, claiming priority to Japanese Patent Application No. 2020-037418, filed Mar. 5, 2020, both of which are herein incorporated by reference in their entirety.

TECHNICAL FIELD

The present disclosure relates generally to an ophthalmic apparatus, a method of controlling the same, and a recording medium.

BACKGROUND OF THE INVENTION

Anterior eye segment analysis techniques using optical coherence tomography (OCT) are known. For example, several techniques of corner angle analysis are disclosed in PATENT DOCUMENTS 1 to 3, and several techniques of corneal thickness analysis are disclosed in PATENT DOCUMENTS 3 and 4.

Generally, image processing called segmentation is used in the field of diagnostic imaging (see, for example, PATENT DOCUMENTS 2 and 4). Segmentation is the process of partitioning a digital image into multiple image segments (multiple image objects) and can also be described as the process of identifying a region with a specific regularity from a digital image. Segmentation is implemented by employing image processing techniques such as thresholding, clustering, region segmentation, edge detection, line segment extraction (line segment detection), or the like. Also, segmentation techniques using machine learning have been put into practical use.

Some typical examples of anterior eye segment analysis use segmentation to identify (extract), from an anterior segment image of an eye, an image object corresponding to a specific part (site, tissue) such as a cornea, an iris, a pupil, or a crystalline lens. For example, some techniques of corner angle analysis identify an image object corresponding to the cornea and an image object corresponding to the iris from an anterior segment image, and define the location where these image objects come in contact with each other as a corner angle position. Also, some techniques of corneal thickness analysis identify an image object corresponding to the anterior surface of the cornea and an image object corresponding to the posterior surface of the cornea from an anterior segment image, and determine the distance between these image objects to be the thickness of the cornea.

As these examples show, segmentation has a significant impact on the quality (e.g., accuracy, precision, reproducibility, etc.) of anterior eye segment analysis. For example, in the case in which segmentation is used to identify an image object corresponding to the cornea from an anterior segment image, this segmentation cannot be performed correctly if an imaginary image (virtual image, inverted image, folded image) of the iris, an image caused by a disturbance such as an eyelash, or a like image overlaps the image object corresponding to the cornea.

FIG. 1A and FIG. 1B illustrate instances of segmentation errors for anterior segment OCT image. The anterior segment image (B-scan image) of FIG. 1A(a) contains the imaginary image 1000 of the iris. FIG. 1A(b) shows the image object (anterior corneal surface image) 1010 corresponding to the anterior corneal surface and the image object (posterior corneal surface image) 1020 corresponding to the posterior corneal surface, which are identified by applying segmentation to the anterior segment image of FIG. 1A(a). As shown in FIG. 1A(c), due to the influence of the contour of the imaginary image 1000 of the iris, the posterior corneal surface image 1020 is deviated from the correct posterior corneal surface image 1040 in the area 1030.

In FIG. 1B(a), an image of an eyelash is depicted in the area 1100 of the anterior segment image (B-scan image). FIG. 1B(b) shows the anterior corneal surface image 1110 and the posterior corneal surface image 1120, which are identified by applying segmentation to the anterior segment image of FIG. 1B(a). Due to the influence of the eyelash image, the anterior corneal surface image 1110 is greatly deviated from the correct anterior corneal surface image 1140 in the area 1130.

PATENT DOCUMENT 1: Japanese Unexamined Patent Application Publication No. 2011-147611
PATENT DOCUMENT 2: Japanese Unexamined Patent Application Publication No. 2013-226383
PATENT DOCUMENT 3: Japanese Unexamined Patent Application Publication (Translation of PCT application) No. 2014-500096
PATENT DOCUMENT 4: Japanese Unexamined Patent Application Publication No. 2017-158728

BRIEF SUMMARY OF THE INVENTION

An object of the present disclosure is to make an improvement in segmentation of anterior segment OCT images.

An ophthalmic apparatus of some aspect examples includes: an image acquiring unit configured to acquire an anterior segment image constructed based on data collected from an anterior segment of a subject's eye by optical coherence tomography (OCT) scanning; a first image region identifying processor configured to identify a first image region corresponding to a predetermined part of the anterior segment by analyzing a first part of the anterior segment image acquired by the image acquiring unit; and a second image region identifying processor configured to identify a second image region corresponding to the predetermined part based on the first image region identified by the first image region identifying processor, the second image region being inside a second part that includes the first part as a proper subset.

The ophthalmic apparatus of some aspect examples further includes: an analysis region setting processor configured to set an analysis region that includes the second image region identified by the second image region identifying processor; and a third image region identifying processor configured to identify a third image region corresponding to the predetermined part by analyzing the analysis region set by the analysis region setting processor.

In the ophthalmic apparatus of some aspect examples, the analysis region setting processor is further configured to set the analysis region by increasing a width of the second image region to a predetermined value.

In the ophthalmic apparatus of some aspect examples, the third image region identifying processor is further configured to identify the third image region by applying edge detection to the analysis region set by the analysis region setting processor.

In the ophthalmic apparatus of some aspect examples, the first image region identifying processor is further configured to identify the first image region by applying edge detection to the first part of the anterior segment image.

In the ophthalmic apparatus of some aspect examples, a threshold value of a gradient value used in the edge detection performed by the third image region identifying processor is smaller than a threshold value of a gradient value used in the edge detection performed by the first image region identifying processor.

In the ophthalmic apparatus of some aspect examples, the second image region identifying processor is further configured to identify the second image region by applying curve fitting to the first image region identified by the first image region identifying processor.

In the ophthalmic apparatus of some aspect examples, the second image region identifying processor is further configured to apply, to the first image region, curve fitting based on a robust estimation algorithm for removing an outlier.

In the ophthalmic apparatus of some aspect examples, the robust estimation algorithm includes a random sample consensus (RANSAC) algorithm.

In the ophthalmic apparatus of some aspect examples, the OCT scanning includes an A-scan and a lateral scan perpendicular to the A-scan, and the ophthalmic apparatus further includes a part setting processor configured to set the first part by setting a part of the anterior segment image that is defined by at least part of an area corresponding to the A-scan and a part of an area corresponding to the lateral scan.

In the ophthalmic apparatus of some aspect examples, the lateral scan includes a B-scan, and the part setting processor is further configured to set the first part by setting a part of the anterior segment image that is defined by the at least part of the area corresponding to the A-scan and an area corresponding to the B-scan with both side regions removed.

In the ophthalmic apparatus of some aspect examples, the part setting processor is further configured to detect a feature point by analyzing the anterior segment image, and to set the first part of the anterior segment image based on the feature point detected.

In the ophthalmic apparatus of some aspect examples, the part setting processor is further configured to detect the feature point by applying edge detection to an entirety of the anterior segment image.

In the ophthalmic apparatus of some aspect examples, the part setting processor is further configured to set the first part in such a manner that the first part includes the feature point.

In the ophthalmic apparatus of some aspect examples, the part setting processor is further configured to apply artifact detection to the anterior segment image, and to set the first part in such a manner that the first part does not include an artifact if the artifact is detected from the anterior segment image.

In the ophthalmic apparatus of some aspect examples, the predetermined part of the anterior segment is a cornea.

In the ophthalmic apparatus of some aspect examples, the first image region identifying processor is further configured to identify a first anterior corneal surface image corresponding to an anterior surface of the cornea and a first posterior corneal surface image corresponding to a posterior surface of the cornea by analyzing the first part of the anterior segment image, and the second image region identifying processor is further configured to identify a second anterior corneal surface image in the second part corresponding to the anterior surface based on the first anterior corneal surface image, and to identify a second posterior corneal surface image in the second part corresponding to the posterior surface based on the first posterior corneal surface image.

The ophthalmic apparatus of some aspect examples further includes: an analysis region setting processor configured to set an anterior surface analysis region that includes the second anterior corneal surface image and a posterior surface analysis region that includes the second posterior corneal surface image; and a third image region identifying processor configured to identify a third anterior corneal surface image corresponding to the anterior surface by analyzing the anterior surface analysis region, and to identify a third posterior corneal surface image corresponding to the posterior surface by analyzing the posterior surface analysis region.

In the ophthalmic apparatus of some aspect examples, the analysis region setting processor is further configured to set the anterior surface analysis region by increasing a width of the second anterior corneal surface image to a predetermined value, and to set the posterior surface analysis region by increasing a width of the second posterior corneal surface image to a predetermined value.

In the ophthalmic apparatus of some aspect examples, the third image region identifying processor is further configured to identify the third anterior corneal surface image by applying edge detection to the anterior surface analysis region, and to identify the third posterior corneal surface image by applying edge detection to the posterior surface analysis region.

In the ophthalmic apparatus of some aspect examples, the first image region identifying processor is further configured to identify the first anterior corneal surface image and the first posterior corneal surface image by applying edge detection to the first part of the anterior segment image.

In the ophthalmic apparatus of some aspect examples, a threshold value of a gradient value used in the edge detection performed by the third image region identifying processor is smaller than a threshold value of a gradient value used in the edge detection performed by the first image region identifying processor.

In the ophthalmic apparatus of some aspect examples, the second image region identifying processor is further configured to identify the second anterior corneal surface image by applying curve fitting to the first anterior corneal surface image, and to identify the second posterior corneal surface image by applying curve fitting to the first posterior corneal surface image.

In the ophthalmic apparatus of some aspect examples, the second image region identifying processor is further configured to apply, to each of the first anterior corneal surface image and the first posterior corneal surface image, curve fitting based on a robust estimation algorithm for removing an outlier.

In the ophthalmic apparatus of some aspect examples, the robust estimation algorithm includes a random sample consensus (RANSAC) algorithm.

In the ophthalmic apparatus of some aspect examples, the OCT scanning includes an A-scan and a lateral scan perpendicular to the A-scan, and the ophthalmic apparatus further includes a part setting processor configured to set the first part by setting a part of the anterior segment image that is defined by at least part of an area corresponding to the A-scan and a part of an area corresponding to the lateral scan.

In the ophthalmic apparatus of some aspect examples, the lateral scan includes a B-scan, and the part setting processor is further configured to set the first part by setting a part of the anterior segment image that is defined by the at least part of the area corresponding to the A-scan and an area corresponding to the B-scan with both side regions removed.

In the ophthalmic apparatus of some aspect examples, the part setting processor is further configured to detect a position corresponding to a corneal apex by analyzing the anterior segment image, and to set the first part of the anterior segment image based on the position corresponding to the corneal apex.

In the ophthalmic apparatus of some aspect examples, the part setting processor is further configured to detect the position corresponding to the corneal apex by applying edge detection to an entirety of the anterior segment image.

In the ophthalmic apparatus of some aspect examples, the part setting processor is further configured to set the first part in such a manner that the first part includes the position corresponding to the corneal apex.

In the ophthalmic apparatus of some aspect examples, the part setting processor is further configured to set the first part in such a manner that the position corresponding to the corneal apex is arranged in a middle position of the lateral scan.

In the ophthalmic apparatus of some aspect examples, the part setting processor is further configured to apply artifact detection to the anterior segment image, and to set the first part in such a manner that the first part does not include an artifact if the artifact is detected from the anterior segment image.

The ophthalmic apparatus of some aspect examples further includes a first image correcting processor configured to correct a distortion of the anterior segment image based at least on the third anterior corneal surface image.

The ophthalmic apparatus of some aspect examples further includes a second image correcting processor configured to correct a pixel aspect ratio of the anterior segment image.

The ophthalmic apparatus of some aspect examples further includes an analyzing processor configured to perform calculation of a predetermined anterior segment parameter by analyzing the anterior segment image.

In the ophthalmic apparatus of some aspect examples, the image acquiring unit includes: a data collector configured to collect data by applying the OCT scanning to the anterior segment; and an image constructing processor configured to construct the anterior segment image based on the data collected by the data collector.

In the ophthalmic apparatus of some aspect examples, the image acquiring unit includes a receiver that receives the anterior segment image from outside.

A method of some aspect examples is a method of controlling an ophthalmic apparatus that includes a processor that includes: causing the processor to acquire an anterior segment image constructed based on data collected from an anterior segment of a subject's eye by optical coherence tomography (OCT) scanning; causing the processor to identify a first image region corresponding to a predetermined part of the anterior segment by analyzing a first part of the anterior segment image; and causing the processor to identify a second image region corresponding to the predetermined part based on the first image region, the second image region being inside a second part that includes the first part as a proper subset.

The method of some aspect examples further includes: causing the processor to set an analysis region that includes the second image region; and causing the processor to identify a third image region corresponding to the predetermined part by analyzing the analysis region.

A program of some aspect examples is a program that causes a computer to execute the method of an aspect example.

A recording medium of some aspect examples is a computer-readable non-transitory recording medium that retains a program of an aspect example.

An aspect example is capable of making an improvement in segmentation of anterior segment OCT images.

BRIEF DESCRIPTION OF THE SEVERAL VIEWS OF THE DRAWING

FIG. 8B is a diagram illustrating an example of a process executed by an ophthalmic apparatus according to an aspect example.

DETAILED DESCRIPTION OF THE INVENTION

Figure 1A:
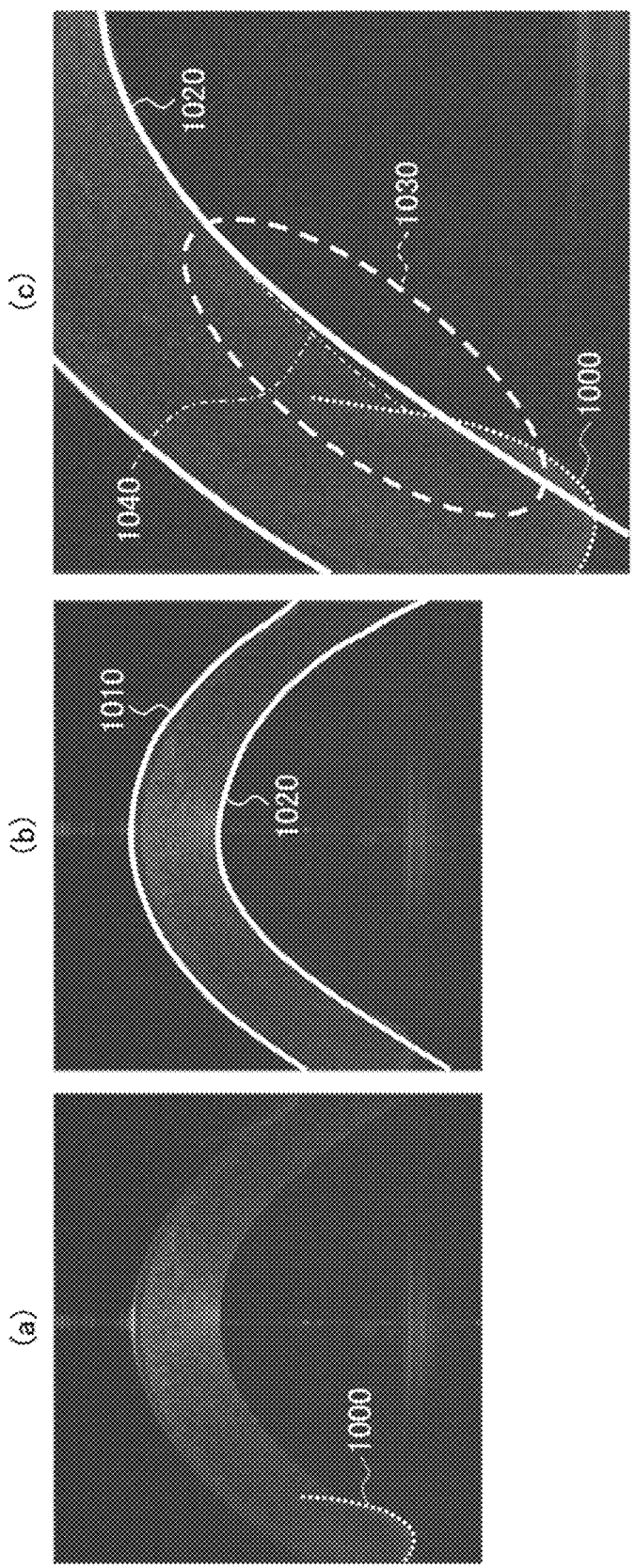
FIG. 1A illustrates an instance of a segmentation error for an anterior segment OCT image.

The present disclosure describes several aspect examples of embodiments of an ophthalmic apparatus, a method of controlling the same, a program, and a recording medium with referring to the drawings. Any matters and items disclosed by the documents cited in the present disclosure and any other known technologies and techniques may be incorporated with the aspect examples described in the present disclosure. Note that "image data" and an "image" formed based on this image data are not distinguished in the present disclosure unless otherwise mentioned. Similarly, a "site (part, tissue, etc.)" of a subject's eye and an "image" of this site are not distinguished in the present disclosure unless otherwise mentioned.

An ophthalmic apparatus according to some aspect examples is configured to be capable of measuring and imaging the anterior segment of a living eye by applying Fourier domain OCT techniques (e.g., swept source OCT techniques). The types of OCT techniques applicable to aspect examples are not limited to swept source OCT techniques, and spectral domain OCT techniques or time domain OCT techniques may be applied to some aspect examples.

An ophthalmic apparatus according to some aspect examples may be configured to be capable of executing processing of an image acquired by a modality other than OCT. For example, some aspect examples may be configured to be capable of executing processing of an image acquired by any of a fundus camera (retinal camera), a laser scanning ophthalmoscope (SLO), a slit lamp microscope, and an ophthalmic surgical microscope. An ophthalmic apparatus according to some aspect examples may include one or more of a fundus camera, an SLO, a slit lamp microscope, and an ophthalmic surgical microscope.

Figure 1B:
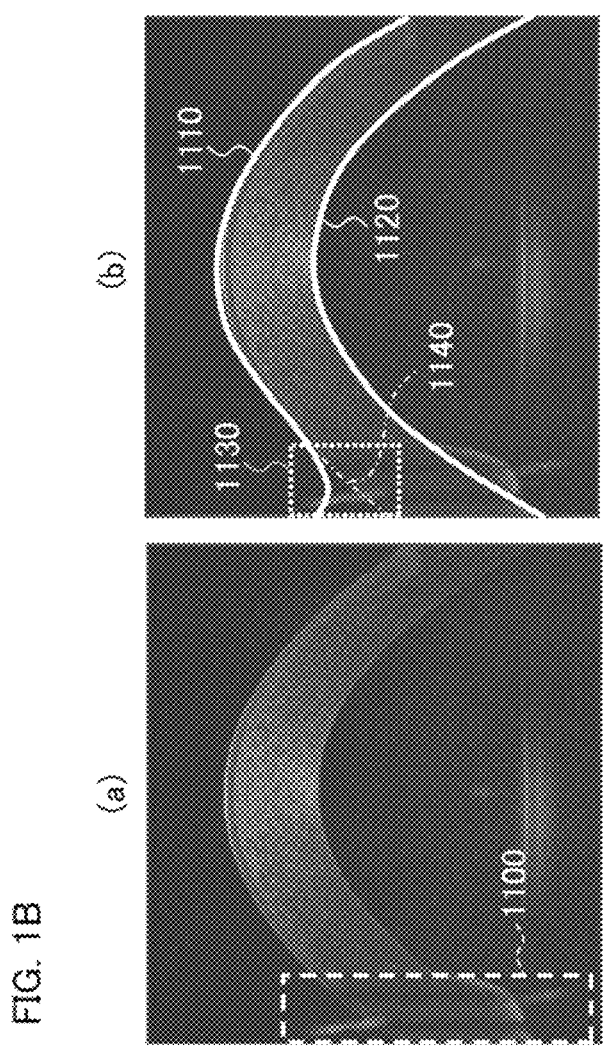
FIG. 1B illustrates an instance of a segmentation error for an anterior segment OCT image.

An ophthalmic apparatus according to some aspect examples is configured to acquire an image constructed based on data collected from the anterior segment of a living eye by applying OCT scanning, and to apply processing to this image. This image is referred to as an anterior segment image. An anterior segment image may contain an artifact such as an imaginary image (virtual image, inverted image, folded image) or an image caused by a disturbance (see, for example, FIG. 1A and FIG. 1B). One of the advantages of aspect examples is the capability to correctly perform segmentation even in the case in which such an artifact exists.

In some aspect examples, the method and technique of acquiring an anterior segment image is freely selected. For example, an ophthalmic apparatus according to some aspect examples may include a configuration of collecting data by applying OCT scanning to the anterior segment of a living eye and a configuration of constructing an anterior segment image based on the data collected.

An ophthalmic apparatus according to some aspect examples may have a function of receiving an anterior segment image of a living eye from outside. In some examples, an anterior segment image of a living eye is acquired by using an OCT apparatus and this anterior segment image is stored in a medical image management system such as a picture archiving and communication system (PACS). An ophthalmic apparatus according to some aspect examples is configured to access the medical image management system and obtain an anterior segment image.

In addition to descriptions of ophthalmic apparatuses according to several aspect examples, the present disclosure gives descriptions of methods of controlling an ophthalmic apparatus according to several aspect examples, descriptions of programs for causing a computer to execute a method of controlling an ophthalmic apparatus according to several aspect examples, and descriptions of recording media according to several aspect examples that retain a program.

At least one or more of the functions of the elements described in the present disclosure are implemented by using a circuit configuration (circuitry) or a processing circuit configuration (processing circuitry). The circuitry or the processing circuitry includes any of the followings, all of which are configured and/or programmed to execute at least one or more functions disclosed herein: a general purpose processor, a dedicated processor, an integrated circuit, a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), an existing or conventional circuit configuration or circuitry, and any combination of these. A processor is considered to be processing circuitry or circuitry that includes a transistor and/or another circuitry. In the present disclosure, circuitry, a unit, a means, or a term similar to these is hardware that executes at least one or more functions disclosed herein, or hardware that is programmed to execute at least one or more functions disclosed herein. Hardware may be the hardware disclosed herein, or alternatively, known hardware that is programmed and/or configured to execute at least one or more functions described herein. In the case in which the hardware is a processor, which may be considered as a certain type of circuitry, then circuitry, a unit, a means, or a term similar to these is a combination of hardware and software. In this case, the software is used to configure the hardware and/or the processor.

<Configuration of Ophthalmic Apparatus>

Figure 2:
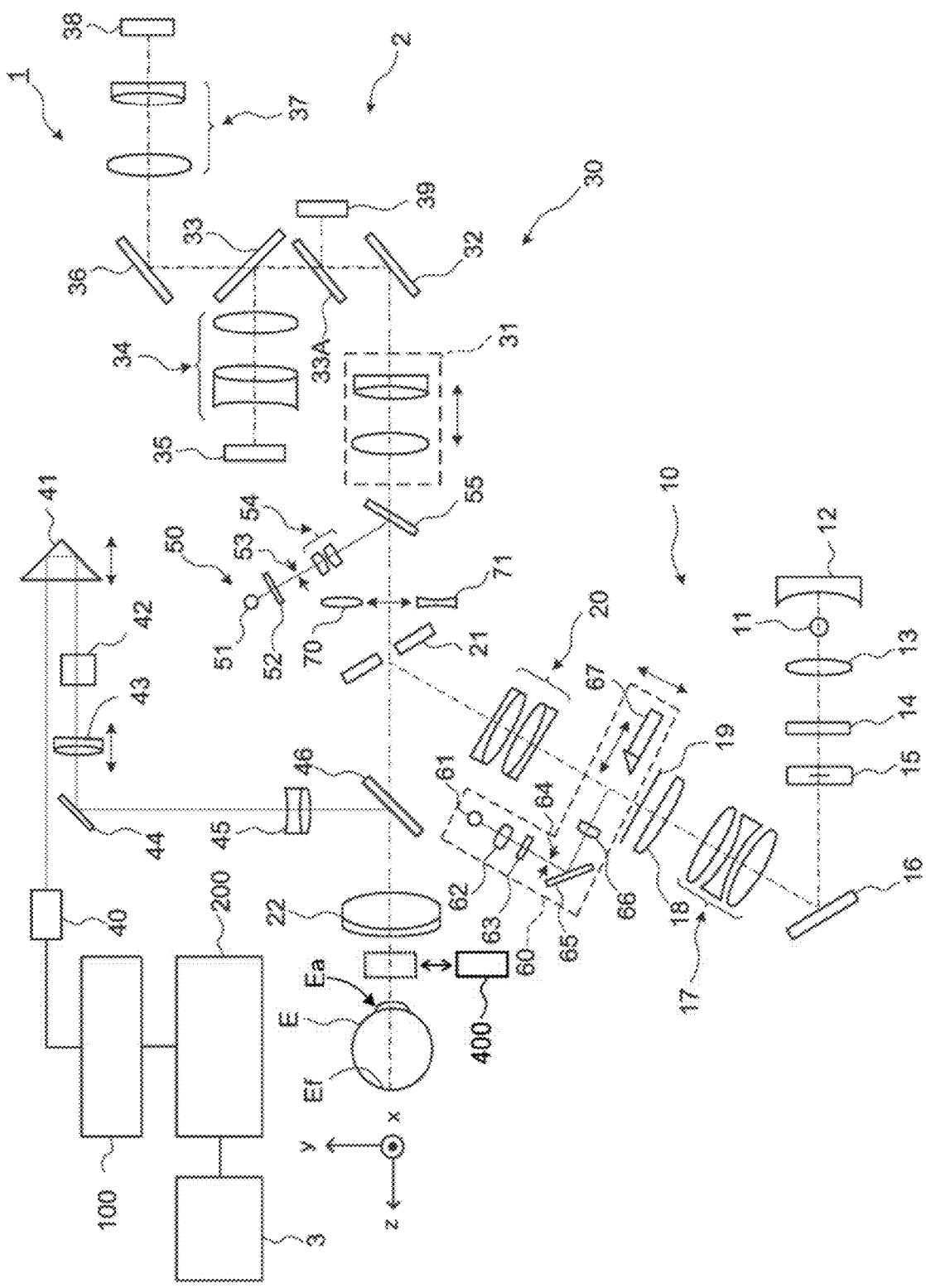
FIG. 2 is a diagram of an example of a configuration of an ophthalmic apparatus according to an aspect example.

The ophthalmic apparatus 1 of an aspect example shown in FIG. 2 is a multifunction apparatus that is a combination of an OCT apparatus and a fundus camera, and has both the function of applying OCT scanning to an anterior eye segment and the function of conducting photography of an anterior eye segment. The ophthalmic apparatus 1 includes the fundus camera unit 2, the OCT unit 100, and the arithmetic and control unit 200. The fundus camera unit 2 is provided with an element group (e.g., optical elements, mechanisms, etc.) for acquiring a front image of a subject's eye. The OCT unit 100 includes part of an element group (e.g., optical elements, mechanisms, etc.) for conducting OCT scanning. Another part of the element group for conducting OCT scanning is provided in the fundus camera unit 2. The arithmetic and control unit 200 includes one or more processors configured and programmed to execute various processes (e.g., calculations, controls, etc.), and one or more storage devices (memories). In addition to these elements, the ophthalmic apparatus 1 may also include any elements and/or any units such as a member for supporting the face of the subject, an attachment for switching or changing sites of a subject's eye to which OCT scanning is applied. Here, examples of the member for supporting the face of the subject include a chin rest and a forehead rest.

A description is now given of some examples of the attachment for switching or changing sites of a subject's eye to which OCT scanning is applied. An example attachment includes a lens group (lens unit). The anterior segment OCT attachment 400 (the attachment for anterior segment OCT 400) of the ophthalmic apparatus 1 of the present aspect example includes a lens group used for switching sites of the subject's eye E to which OCT scanning is applied between the posterior segment and the anterior segment. The anterior segment OCT attachment 400 may have the same configuration as the optical unit disclosed in Japanese Unexamined Patent Application Publication No. 2015-160103.

As illustrated in FIG. 2, the anterior segment OCT attachment 400 is inserted between the objective lens 22 and the subject's eye E. In the state in which the anterior segment OCT attachment 400 is placed in the optical path, the ophthalmic apparatus 1 can apply OCT scanning to the anterior segment of the subject's eye E. On the other hand, in the state in which the anterior segment OCT attachment 400 is removed from the optical path, the ophthalmic apparatus 1 can apply OCT scanning to the posterior segment of the subject's eye E. The movement (insertion and removal) of the anterior segment OCT attachment 400 is performed by hand or by machine (manually or automatically).

An ophthalmic apparatus of some aspect examples may be configured to apply OCT scanning to a posterior segment in the state in which an attachment is inserted in an optical path and to apply OCT scanning to an anterior segment in the state in which this attachment is removed from this optical path. Sites of a subject's eye to which OCT scanning is applied switched by an attachment are not limited to the combination of anterior segment and posterior segment, and may be any combinations of ocular sites. Also, a configuration for switching sites of a subject's eye to which OCT scanning is applied is not limited to attachments like the one described above (lens group, lens unit, optical unit), and some examples of this configuration may include one or more lenses movable along an optical path.

<Fundus Camera Unit 2>

The fundus camera unit 2 includes elements (e.g., optical elements, mechanisms, etc.) for acquiring digital images (digital photographs, digital pictures) by conducting photography of the subject's eye E (e.g., the anterior segment Ea, fundus Ef, etc.). The digital images of the subject's eye E acquired are front images (en face images) such as observation images and photographed images. An observation image is obtained, for example, by capturing a moving image using near-infrared light, and may be used for alignment, focusing, tracking, and other operations. A photographed image is a still image obtained using visible flash light or infrared flash light, for example. A photographed image may be used for diagnosis, analysis, or other purposes.

The fundus camera unit 2 includes the illumination optical system 10 and the photographing optical system 30. The illumination optical system 10 projects illumination light onto the subject's eye E. The photographing optical system 30 detects return light of the illumination light from the subject's eye E. Measurement light entered from the OCT unit 100 is directed to the subject's eye E through an optical path in the fundus camera unit 2, and return light of this measurement light from the subject's eye E is directed to the OCT unit 100 through the same optical path.

Light emitted by the observation light source 11 of the illumination optical system 10 (referred to as observation illumination light) is reflected by the concave mirror 12, passes through the condenser lens 13, and becomes near-infrared light after passing through the visible cut filter 14. Further, the observation illumination light is once converged at a location near the photographing light source 15, reflected by the mirror 16, and passes through the relay lens system 17, the relay lens 18, the diaphragm 19, and the relay lens system 20. Then, the observation illumination light is reflected on the peripheral part (i.e., the area surrounding the aperture part) of the aperture mirror 21, penetrates the dichroic mirror 46, and refracted by the objective lens 22, thereby illuminating the subject's eye E. Return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Furthermore, the return light of the observation illumination light passes through the half mirror 33A, is reflected by the dichroic mirror 33, and forms an image on the light receiving surface of the image sensor 35 by the imaging lens 34. The image sensor 35 detects the return light at a predetermined frame rate. The photographing optical system 30 is adjusted to be focused on the fundus Ef or the anterior eye segment Ea.

Light emitted by the photographing light source 15 (referred to as photographing illumination light) passes through the same route as the route of the observation illumination light and is projected onto the subject's eye E. Return light of the photographing illumination light from the subject's eye E passes through the same route as the route of the return light of the observation illumination light to the dichroic mirror 33, passes through the dichroic mirror 33, is reflected by the mirror 36, and forms an image on the light receiving surface of the image sensor 38 by the imaging lens 37.

The liquid crystal display (LCD) 39 displays a fixation target (fixation target image). Part of a light beam output from the LCD 39 is reflected by the half mirror 33A and the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef.

Varying the display position of the fixation target image on the LCD 39 can be used to change fixation position (also referred to as fixation direction) of the subject's eye E by the fixation target. That is, the line of sight of the subject's eye E can be guided in a desired direction by changing the fixation position. The ophthalmic apparatus 1 may be provided with a graphical user interface (GUI) used for designation of a desired fixation position.

Configurations for presenting, to the subject's eye E, a fixation target in such a manner that a fixation position can be changed, are not limited to a display device such as LCD. For example, a fixation matrix may be used, in place of such a display device, that includes a plurality of light emitting elements (e.g., light emitting diodes or the like) arranged in a matrix pattern (array pattern). In this example case, a fixation position can be changed by selecting and turning on a light emitting element. In another example case, a fixation position can be changed by means of one or more movable light emitting elements.

The alignment optical system 50 generates an alignment indicator used for alignment of the optical system with respect to the subject's eye E. Alignment light emitted by the light emitting diode (LED) 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. Return light of the alignment light from the subject's eye E passes through the same route as the route of the return light of the observation illumination light and is guided to the image sensor 35. An image detected by the image sensor 35 (alignment indicator image) is used for performing manual alignment and/or automatic alignment.

As in existing or conventional techniques, the alignment indicator image of the present example includes two bright spot images whose positions change depending on alignment states (alignment conditions). When the relative position between the subject's eye E and the optical system changes in the xy direction, the two bright spot images are shifted together in the xy direction. When the relative position between the subject's eye E and the optical system changes in the z direction, the relative position (the distance)

between the two bright spot images changes. In the state in which the distance between the subject's eye E and the optical system in the z direction matches with a working distance set in advance, the two bright spot images overlap each other. In the state in which the position of the subject's eye E matches with the position of the optical system in the xy direction, the two bright spot images are located within or near an alignment target set in advance. In the state in which not only the distance between the subject's eye E and the optical system in the z direction matches with the working distance but also the position of the subject's eye E matches with the position of the optical system in the xy direction, the two bright spot images overlap each other and are located within the alignment target.

When conducting automatic alignment, the data processor 230 detects the positions of the two bright spot images, and the main controller 211 controls the movement mechanism 150 (described later) on the basis of the positional relationship between the two bright spot images and the alignment target. When conducting manual alignment, the main controller 211 displays the two bright spot images together with an observation image of the subject's eye E on the display 241, and the user manipulates the operation device 242 to operate the movement mechanism 150 while monitoring the two bright spot images displayed.

The methods and techniques of alignment are not limited to those described above. An ophthalmic apparatus according to some aspect examples may include an alignment unit configured to perform the following processes (see, for example, Japanese Unexamined Patent Application Publication No. 2013-248376); a process of acquiring two or more photographed images of an anterior segment of a subject's eye by substantially simultaneously conducting two or more operations of anterior segment photography of the anterior segment from two or more different directions; a process of calculating a three dimensional position of the subject's eye by analyzing the two or more photographed images; and a process of moving an optical system based on the three dimensional position calculated.

The focusing optical system 60 generates a split indicator used for focus adjustment (focusing, focusing operation) with respect to the subject's eye E. The focusing optical system 60 is moved along the optical path of the illumination optical system 10 in conjunction with movement of the photography focusing lens 31 along the optical path of the photographing optical system 30. The optical path of the illumination optical system 10 is referred to as the illumination optical path, and the optical path of the photographing optical system 30 is referred to as the photographing optical path. The reflection rod 67 is inserted into and removed from the illumination optical path. The reflective surface of the reflection rod 67 is inserted into the illumination optical path and placed in an oblique orientation before performing focus adjustment. Focus light emitted by the LED 61 passes through the relay lens 62, is split into two light beams by the split indicator plate 63, and passes through the two-hole diaphragm 64. The focus light, then, is reflected by the mirror 65, is converged on the reflective surface of the reflection rod 67 by the condenser lens 66, and is reflected by the reflective surface. Further, the focus light travels through the relay lens 20, is reflected by the aperture mirror 21, and penetrates the dichroic mirror 46, thereby being projected onto the subject's eye E via the objective lens 22. Return light of the focus light from the subject's eye E passes through the same route as the route of the return light of the alignment light and is guided to the image sensor 35.

An image detected by the image sensor 35 (split indicator image) is used for performing manual focusing and/or automatic focusing.

The diopter correction lenses 70 and 71 are selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for digital photography and the optical path for OCT scanning. The optical path for digital photography includes the illumination optical path and the photographing optical path. The optical path for OCT scanning is referred to as a sample arm. The dichroic mirror 46 reflects light of wavelength bands used for OCT scanning while transmitting light for digital photography. Listed from the OCT unit 100 side, the sample arm includes the collimator lens unit 40, the retroreflector 41, the dispersion compensation member 42, the OCT focusing lens 43, the optical scanner 44, and the relay lens 45.

The retroreflector 41 is movable in the directions indicated by the arrow in FIG. 2. These directions are the direction in which the measurement light LS is incident onto the subject's eye E and the direction in which return light of the measurement light LS from the subject's eye E travels. With this movement of the retroreflector 41, the length of the sample arm is changed. This change in the sample arm length may be used for operations such as optical path length correction on the basis of eye axial length, optical path length correction on the basis of corneal shape and/or eye fundus shape, and adjustment or regulation of interference conditions or states.

The dispersion compensation member 42, together with the dispersion compensation member 113 (described later) arranged in the reference arm, acts to equalize the dispersion characteristics of the measurement light LS and the dispersion characteristics of the reference light LR with each other.

The OCT focusing lens 43 is movable in the directions indicated by the arrow in FIG. 2 (that is, movable along the optical axis of the sample arm) in order to perform focus adjustment of the sample arm. With this movement of the OCT focusing lens 43, the focus conditions or the focus states (focal position, focal length) of the sample arm is changed. The ophthalmic apparatus 1 may be configured to be capable of executing interlocking control between the movement of the photography focusing lens 31, the movement of the focusing optical system 60, and the movement of the OCT focusing lens 43.

The optical scanner 44 is placed substantially at a position optically conjugate with the pupil of the subject's eye E. The optical scanner 44 deflects the measurement light LS guided by the sample arm. The optical scanner 44 of some examples may be a deflection system capable of two dimensional scanning that includes a deflector for performing scanning in the x direction and a deflector for performing scanning in the y direction (x-scanner and y-scanner). The optical scanner 44 of some examples may be a galvanometer scanner including two galvanometer mirrors. In some typical examples, one of the two deflectors is arranged at a position optically conjugate with the pupil of the subject's eye E, or the position optically conjugate with the pupil is arranged at a position between the two deflectors. Such arrangement makes it capable of OCT scanning of the fundus Ef in which the measurement light LS is deflected around a pivot located at a position in (or near) the pupil of the subject's eye E, which makes it possible to apply OCT scanning to a wide (broad) area of the fundus Ef.

In the present aspect example, the optical scanner 44 is placed at a position substantially optically conjugate with the pupil of the subject's eye E as described above when the anterior segment OCT attachment 400 is not placed in the optical path. On the other hand, the optical scanner 44 is placed at a position substantially optically conjugate with a position between the anterior segment Ea and the anterior segment OCT attachment 400 when the anterior segment OCT attachment 400 is placed in the optical path. More specifically, in the case in which the anterior segment OCT attachment 400 is removed from the optical path, for example, one of the x-scanner and the y-scanner is placed at a position substantially optically conjugate with the pupil, or a position between the x-scanner and the y-scanner is placed at a position substantially optically conjugate with the pupil. Further, in the case in which the anterior segment OCT attachment 400 is inserted in the optical path, for example, one of the x-scanner and the y-scanner is placed at a position substantially optically conjugate with a position between the anterior segment Ea and the anterior segment OCT attachment 400, or a position between the x-scanner and the y-scanner is placed at a position substantially optically conjugate with a position between the anterior segment Ea and the anterior segment OCT attachment 400.

<OCT Unit 100>

Figure 3:
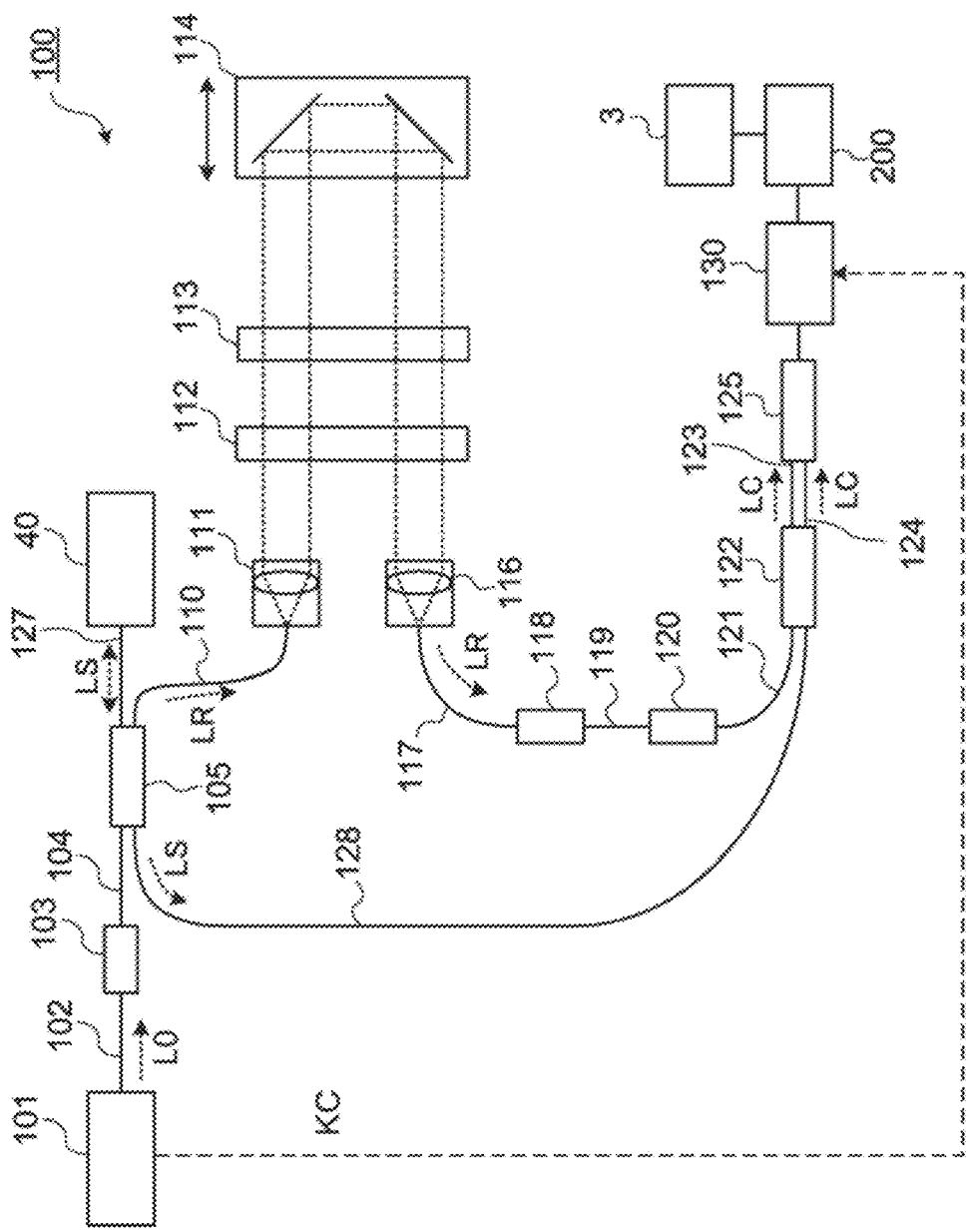
FIG. 3 is a diagram of an example of a configuration of an ophthalmic apparatus according to an aspect example.

As illustrated in FIG. 3, the OCT unit 100 is provided with an optical system and mechanisms for performing swept source OCT. This optical system includes an interference optical system. This interference optical system is configured to split light emitted by a wavelength tunable light source (wavelength sweeping light source) into measurement light and reference light, to generate interference light by superposing return light of the measurement light from the subject's eye E on the reference light that has been guided by a reference optical path (reference arm), and to detect this interference light. A result of this interference light detection (detection signal) obtained by the interference optical system, is a signal representing a spectrum of the interference light (interference signal). This detection signal is sent to the arithmetic and control unit 200 (the image data constructing unit 220).

The light source unit 101 of some examples includes a near-infrared wavelength tunable laser configured to vary the wavelengths of emitted light at high speed. The light LO output from the light source unit 101 is guided to the polarization controller 103 through the optical fiber 102. The polarization controller 103 is configured to perform regulation (adjustment) of the polarization condition (polarization state) of the light LO. Further, the light LO is guided to the fiber coupler 105 through the optical fiber 104. The fiber coupler 105 is configured to split the light LO into the measurement light LS and the reference light LR. The optical path of the measurement light LS is referred to as the sample arm or the like, and the optical path of the reference light LR is referred to as the reference arm or the like.

The reference light LR is guided through the optical fiber 110 to the collimator 111, is converted into a parallel light beam by the collimator 111, travels through the optical path length correction member 112 and the dispersion compensation member 113, and is guided to the retroreflector 114. The optical path length correction member 112 is an optical element for equalizing the optical path length of the reference light LR and the optical path length of the measurement light LS with each other. The dispersion compensation member 113 is an optical element for equalizing the dispersion characteristics of the reference light LR and the dispersion characteristics of the measurement light LS with each other, together with the dispersion compensation member 42 disposed in the sample arm. The retroreflector 114 is movable along the optical path of the reference light LR that is incident onto the retroreflector 114. With this, the length of the reference arm is changed. This change in the reference arm length may be used for operations such as optical path length correction on the basis of eye axial length, optical path length correction on the basis of corneal shape and/or eye fundus shape, and adjustment or regulation of interference conditions or states.

The reference light LR that has passed through the retroreflector 114 travels through the dispersion compensation member 113 and the optical path length correction member 112, is converted from a parallel light beam to a convergent light beam by the collimator 116, and is incident onto the optical fiber 117. The reference light LR that has entered the optical fiber 117 is guided to the polarization controller 118, and the polarization state of the reference light LR is regulated by the polarization controller 118. The polarization controller 118 is an optical device for interference condition regulation (interference condition adjustment, interference state regulation, interference state adjustment). The polarization controller 118 is used for optimizing the strength of interference (coherence) between the measurement light LS and the reference light LR, for example. The reference light LR output from the polarization controller 118 is guided to the attenuator 120 through the optical fiber 119, and the amount of light of the reference light LR is regulated by the attenuator 120. Subsequently, the reference light LR is guided to the fiber coupler 122 through the optical fiber 121.

Meanwhile, the measurement light LS generated by the fiber coupler 105 is guided through the optical fiber 127 to the collimator lens unit 40 and is converted to a parallel light beam by the collimator lens unit 40. The measurement light LS output from the collimator lens unit 40 passes through the retroreflector 41, the dispersion compensation member 42, the OCT focusing lens 43, the optical scanner 44, and the relay lens 45, is reflected by the dichroic mirror 46, and is refracted by the objective lens 22, thereby being projected onto the subject's eye E. The measurement light LS is reflected and scattered at various depth positions of the subject's eye E. Return light of the measurement light LS from the subject's eye E travels along the same route as the outward way in the opposite direction to the fiber coupler 105, and then reaches the fiber coupler 122 through the optical fiber 128.

The fiber coupler 122 superposes the measurement light LS reached here through the optical fiber 128 with the reference light LR reached here through the optical fiber 121 to generate interference light. The fiber coupler 122 splits the interference light generated by the fiber coupler 122 at a predetermined splitting ratio (e.g., 1 to 1) to generate a pair of interference light LC. The pair of interference light LC is guided to the detector 125 through the optical fibers 123 and 124, respectively.

The detector 125 of some examples includes a balanced photo diode. This balanced photodiode includes a pair of photodetectors that detects the pair of the interference light LC respectively. The balanced photodiode outputs a difference signal between a pair of detection signals corresponding to the pair of the interference light LC respectively obtained by the pair of photodetectors. The detector 125 sends this output (difference signal, detection signal) to the data acquisition system (DAQ) 130.

The clock KC is supplied from the light source unit 101 to the data acquisition system 130. The clock KC is generated in the light source unit 101 in synchronization with the output timings of individual wavelengths varied over a predetermined wavelength range by the wavelength tunable light source. The light source unit 101 of some examples is configured to split the light LO of the individual output wavelengths to generate two pieces of split light, to apply an optical delay to one of the two pieces of split light, to superpose the resulting two pieces of split light with one another, to detect the resulting superposed light, and to generate the clock KC based on the detection result of the superposed light. Based on the clock KC, the data acquisition system 130 performs sampling of the detection signal input from the detector 125. The data acquisition system 130 sends the result of this sampling to the arithmetic and control unit 200.

The present aspect example is provided with both an element for changing the sample arm length (e.g., the retroreflector 41) and an element for changing the reference arm length (e.g., the retroreflector 114 or a reference mirror). However, some other aspect examples may be provided with only either one of these two elements. An element for changing the difference between the sample arm length and the reference arm length (i.e., an element for changing the optical path length difference) is not limited to these examples described herein, and may be freely selected element such as any optical member and/or any mechanism.

As described above, swept source OCT is a technique including the following processes: a process of splitting light emitted by a wavelength tunable light source into measurement light and reference light; a process of generating interference light by superposing return light of the measurement light from a sample and the reference light; a process of detecting the interference light by a photodetector; and a process of constructing an image of the sample by applying signal processing including a Fourier transform to detection data collected corresponding to wavelength sweeping (change in emitted wavelengths) and scanning with the measurement light.

Spectral domain OCT, an alternative to swept source OCT, is a technique including the following processes: a process of splitting light emitted by a low coherence light source (broad band light source, wide band light source) into measurement light and reference light; a process of generating interference light by superposing return light of the measurement light from a sample and the reference light; a process of detecting a spectral distribution (spectral components) of the interference light by a spectrometer; and a process of constructing an image of the sample by applying signal processing including a Fourier transform to the spectral distribution detected.

In short, swept source OCT can be said to be an OCT technique of acquiring a spectral distribution of interference light in a time-divisional manner while spectral domain OCT can be said to be an OCT technique of acquiring a spectral distribution of interference light in a space-divisional manner.

<Control System and Processing System>

Figure 4:
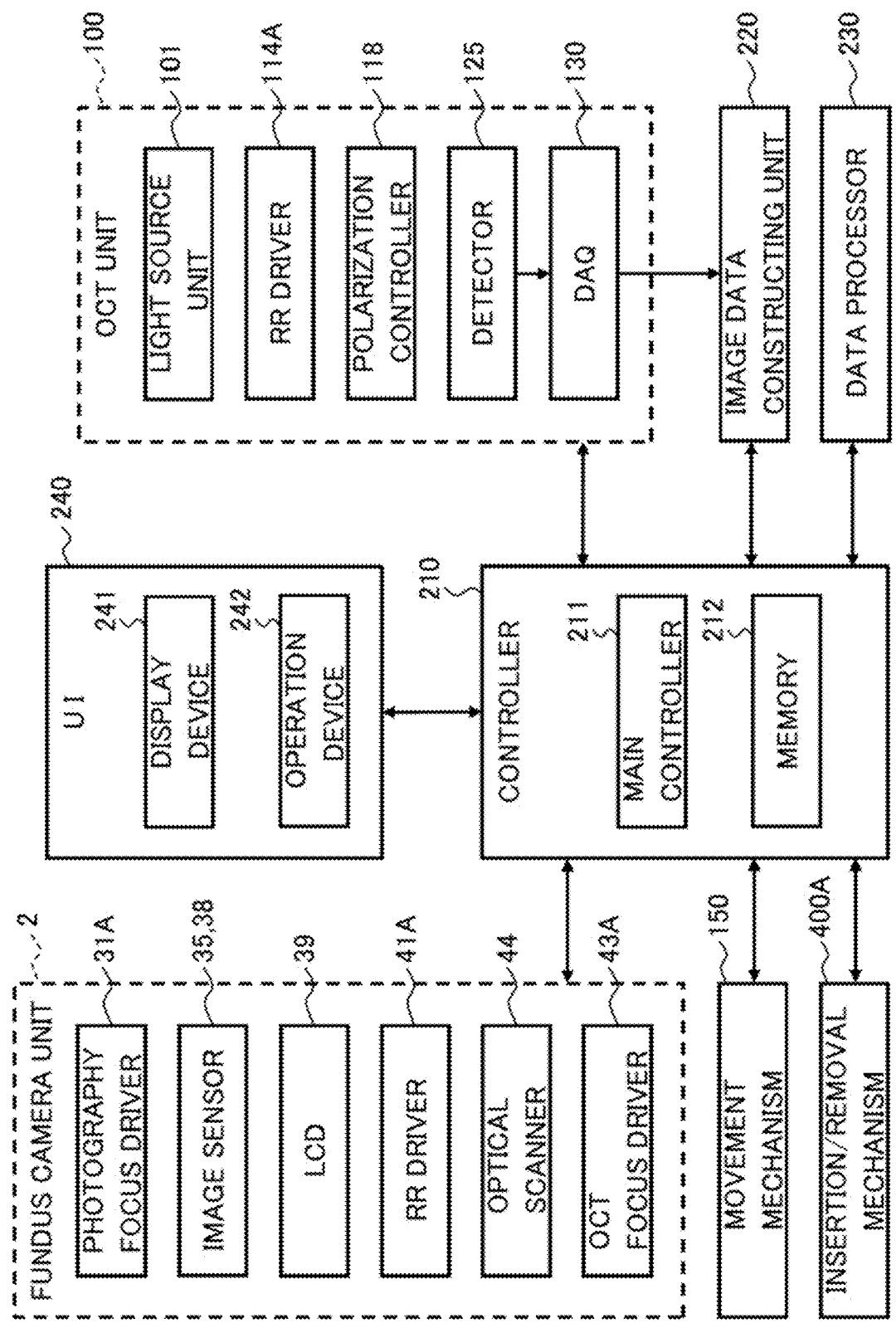
FIG. 4 is a diagram of an example of a configuration of an ophthalmic apparatus according to an aspect example.
Figure 5:
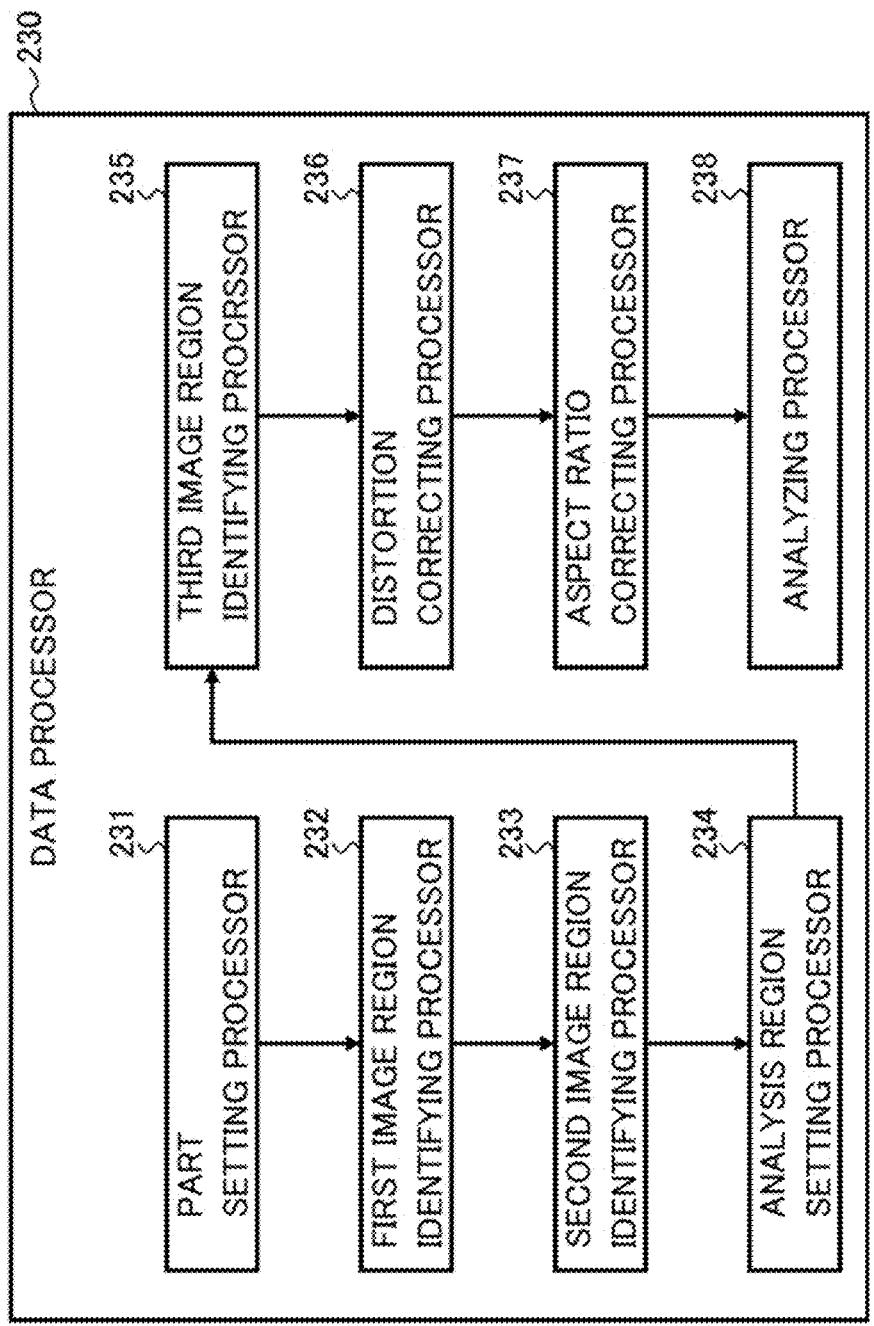
FIG. 5 is a diagram of an example of a configuration of an ophthalmic apparatus according to an aspect example.

FIG. 4 and FIG. 5 illustrate examples of the configurations of the control system and the processing system of the ophthalmic apparatus 1. The arithmetic and control unit 200 of some examples may include the controller 210, the image data constructing unit 220, and the data processor 230. The ophthalmic apparatus 1 may further include a communication device for performing data communication with external apparatuses. The ophthalmic apparatus 1 may further include a drive device (reader and/or writer) for reading out data from recording media and writing data into recording media.

<Controller 210>

The controller 210 performs various kinds of controls. The controller 210 includes the main controller 211 and the memory 212. The main controller 211 includes one or more processors and executes control of each element of the ophthalmic apparatus 1 (including the elements shown in FIG. 2 to FIG. 5). The main controller 211 is implemented by cooperation between hardware including the one or more processors and control software.

The photography focus driver 31A is configured to move the photography focusing lens 31 disposed in the photographing optical path and the focusing optical system 60 disposed in the illumination optical path under control of the main controller 211. The retroreflector driver (RR driver) 41A is configured to move the retroreflector 41 disposed in the sample arm under control of the main controller 211. The OCT focus driver 43A is configured to move the OCT focusing lens 43 disposed in the sample arm under control of the main controller 211. The retroreflector driver (RR driver) 114A is configured to move the retroreflector 114 disposed in the reference arm under control of the main controller 211. Each of the above drivers includes an actuator, such as a pulse motor, that operates under control of the main controller 211. The optical scanner 44 disposed in the sample arm also operates under control of the main controller 211.

The movement mechanism 150 of some examples is configured to move the fundus camera unit 2 in a three dimensional manner. The movement mechanism 150 of some typical examples includes the following elements: an x stage that is movable in the ±x directions (left and right directions); an x movement mechanism configured to move the x stage; a y stage that is movable in the ±y directions (upward and downward directions); a y movement mechanism configured to move the y stage; a z stage that is movable in the ±z directions (front and back directions, depth direction); and a z movement mechanism configured to move the z stage. Each of these movement mechanisms includes an actuator, such as a pulse motor, that operates under control of the main controller 211.

The insertion and removal mechanism 400A is configured to perform an operation of inserting the anterior segment OCT attachment 400 into the OCT optical path (sample arm), and an operation of removing the anterior segment OCT attachment 400 from the OCT optical path (sample arm). The insertion and removal mechanism 400A includes an actuator, such as a solenoid actuator, that operates under control of the main controller 211.

The memory 212 retains various kinds of data. Examples of data stored in the memory 212 include OCT images, digital images (anterior segment images, fundus images), subject's eye information, and analysis data. The subject's eye information includes subject information such as a patient identifier (patient ID) and a patient's name, identification information for right and left eyes, and electronic medical record information.

<Image Data Constructing Unit 220>

The image data constructing unit 220 includes one or more processors and is configured to construct OCT image data of the subject's eye E based on signals (sampling data) input from the data acquisition system 130. The OCT image data constructed by the image data constructing unit 220 is one or more pieces of A-scan image data, and typically is B-scan image data (two dimensional cross sectional image data, two dimensional tomographic image data) consisting of a plurality of pieces of A-scan image data.

The process of constructing OCT image data includes noise elimination (noise reduction), filtering, fast Fourier transform (FFT), and other processes, as in existing or conventional Fourier domain OCT techniques. In the cases in which other types of OCT techniques are employed, the image data constructing unit 220 executes known processing in accordance with an OCT technique employed.

The image data constructing unit 220 may be configured to construct three dimensional data of the subject's eye E based on signals input from the data acquisition system 130. This three dimensional data is three dimensional image data representing a three dimensional region (referred to as a volume) of the subject's eye E. This three dimensional image data is image data in which the positions of pixels are defined using a three dimensional coordinate system. Examples of such three dimensional image data include stack data and volume data.

Stack data is image data formed by arranging (disposing), in a three dimensional manner, a plurality of cross sectional images acquired along a plurality of scan lines, on the basis of the positional relationship between these scan lines. In other words, stack data is image data constructed by representing multiple cross sectional images, which are originally defined in individually different two dimensional coordinate systems, with a single three dimensional coordinate system, that is, by embedding the multiple cross sectional images into a single three dimensional space. In further other words, stack data is image data formed by arranging, in a three dimensional manner, a plurality of A-scan image data acquired respectively for a plurality of scan points arranged in a two dimensional manner (that is, for a scan point array), on the basis of the positional relationship between these scan points.

Volume data is image data whose elements (picture elements) are voxels arranged in a three dimensional manner. Volume data is also referred to as voxel data, volume data is constructed by applying processing such as interpolation and voxelization to stack data.

The image data constructing unit 220 constructs an image for display, by applying rendering to three dimensional image data. Examples of applicable rendering techniques include volume rendering, surface rendering, maximum intensity projection (MIP), minimum intensity projection (MinIP), and multi planar reconstruction (MPR).

The image data constructing unit 220 may be configured to construct an OCT front image (OCT en face image) based on three dimensional image data. The image data constructing unit 220 of some examples may be configured to construct projection data of three dimensional image data by applying, to the three dimensional image data, projection processing in the z direction (A-line direction, depth direction). Similarly, the image data constructing unit 220 may be configured to construct projection data from partial data of three dimensional image data such as a slab of three dimensional image.

In some typical examples, partial data of three dimensional image data, such as a slab, may be obtained by using segmentation processing. Segmentation, or image segmentation, is an image processing technique of partitioning an image to identify a partial region. Segmentation of some typical examples is performed to identify an image region corresponding to a predetermined tissue of the subject's eye E. Segmentation of some examples may include any known image processing techniques, and may include, for example, image processing such as edge detection and/or a segmentation technique using machine learning (e.g., deep learning). Segmentation of the present aspect example is executed, for example, by the image data constructing unit 220 or the data processor 230.

Note that the data processor 230 of the present aspect example is configured to be capable of executing the segmentation as described later, and has an advantageous feature that is capable of executing segmentation of an anterior segment image even though the anterior segment image contains an artifact.

The ophthalmic apparatus 1 may be capable of performing OCT motion contrast imaging. OCT motion contrast imaging is a technique of imaging motion of fluid (liquid) etc. in an eye (see, for example, Japanese Unexamined Patent Application Publication (Translation of PCT application) No. 2015-515894).

The image data constructing unit 220 is implemented by cooperation between hardware including one or more processors and image data constructing software.

<Data Processor 230>

The data processor 230 includes one or more processors and is configured to perform various kinds of data processing on an image of the subject's eye E. The data processor 230 of some examples is implemented by cooperation between hardware including the one or more processors and data processing software.

The data processor 230 may be configured to perform position matching (registration) between two images acquired for the subject's eye E. The data processor 230 of some examples may be configured to perform registration between three dimensional image data acquired using OCT scanning and a front image (en face image) acquired by the fundus camera unit 2. The data processor 230 of some examples may be configured to perform registration between two OCT images acquired using OCT scanning. The data processor 230 of some examples may be configured to perform registration between two front images acquired by the fundus camera unit 2. The data processor 230 of some examples may be configured to apply registration to any of resulting data of analysis of one or more OCT images, resulting data of analysis of one or more front images, and other analysis results. Registration may be performed using freely selected known techniques. Registration of some examples may include feature point extraction and affine transformation.

As mentioned above, the data processor 230 includes a configuration for performing correct segmentation on an anterior segment image contaminated by an artifact. FIG. 5 shows an example of the configuration of the data processor 230. The data processor 230 of the present example includes at least the first image region identifying processor 232 and the second image region identifying processor 233. Further, the data processor 230 of the present example may include the analysis region setting processor 234 and the third image region identifying processor 235. In addition, the data processor 230 of the present example may include one or more of the part setting processor 231, the distortion correcting processor 236, the aspect ratio correcting processor 237, and the analyzing processor 238.

In the present example, suppose that an anterior segment image processed by the data processor 230 is an image obtained by using OCT scanning that is a combination of an A-scan and a lateral scan. An A-scan is a scan in the depth direction (axial direction), and a lateral scan is a scan in a direction perpendicular to the A-scan. Note that a lateral scan is performed by the optical scanner 44. In some typical examples, an anterior segment image processed by the data processor 230 may be one or more B-scan images, three dimensional image, or one or more circle scan images. While the following describes in detail the case in which one B-scan image is processed, other types of anterior segment images can be processed in the same or similar manner.

<Part Setting Processor 231>

The part setting processor 231 is configured to perform identification of a part of an anterior segment image that is defined by both at least part of an area corresponding to an A-scan (A-scan area) and at least part of an area corresponding to a lateral scan (lateral scan area). The part of the anterior segment image identified by the part setting processor 231 is to be analyzed by the first image region identifying processor 232 in a later step. The part of the anterior segment image set by the part setting processor 231 is referred to as the first part.

Figure 6:
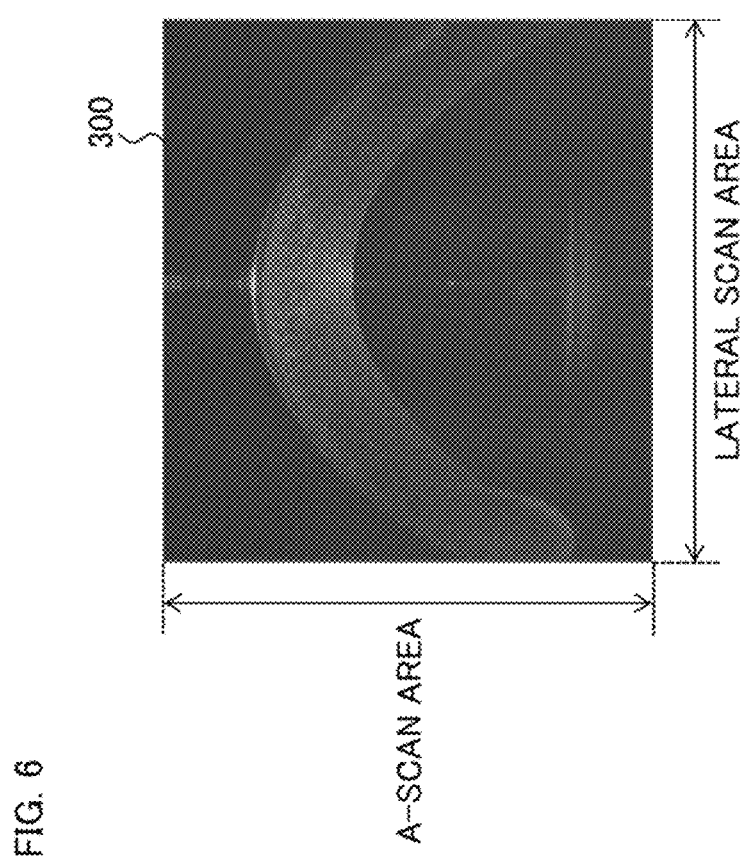
FIG. 6 is a diagram illustrating an example of a process executed by an ophthalmic apparatus according to an aspect example.

Here, an A-scan area corresponds to an imaging area (imaging range, imaging region; area in which an image is constructed) in the depth direction (z direction) (see the anterior segment image 300 shown in FIG. 6). An A-scan area is set in advance. Also, a lateral scan area corresponds to an imaging area in the direction (lateral direction) in which the measurement light LS is moved (carried) by the optical scanner 44 (see the anterior segment image 300 of FIG. 6). A lateral scan area may be determined on the basis of a scan mode set in advance. Examples of the scan mode include a scan pattern, a scan length (angle of view: standard angle, wide angle, or the like).

The extent of the area in the depth direction of the first part of the anterior segment image set by the part setting processor 231 is a part or the entirety of the A-scan area, and the extent of the area in the lateral direction of the first part is (only) a part of the lateral scan area (the extent of the area in the lateral direction of the first part is not the entirety of the lateral scan area). In other words, while the extent of the area in the depth direction of the first part of the anterior segment image set by the part setting processor 231 may be a part of the A-scan area or the entire A-scan area, the extent of the area in the lateral direction of the first part is an area of the lateral scan area with a partial area thereof removed.

In some aspect examples, in the case in which OCT scanning for anterior segment image acquisition is a lateral scan that includes a B-scan such as a B-scan, a three dimensional scan (volume scan), or a radial scan, the part setting processor 231 may set, to the first part, a part of an anterior segment image defined by at least part of the A-scan area and by a part of the B-scan area with both side regions removed.

Figure 7:
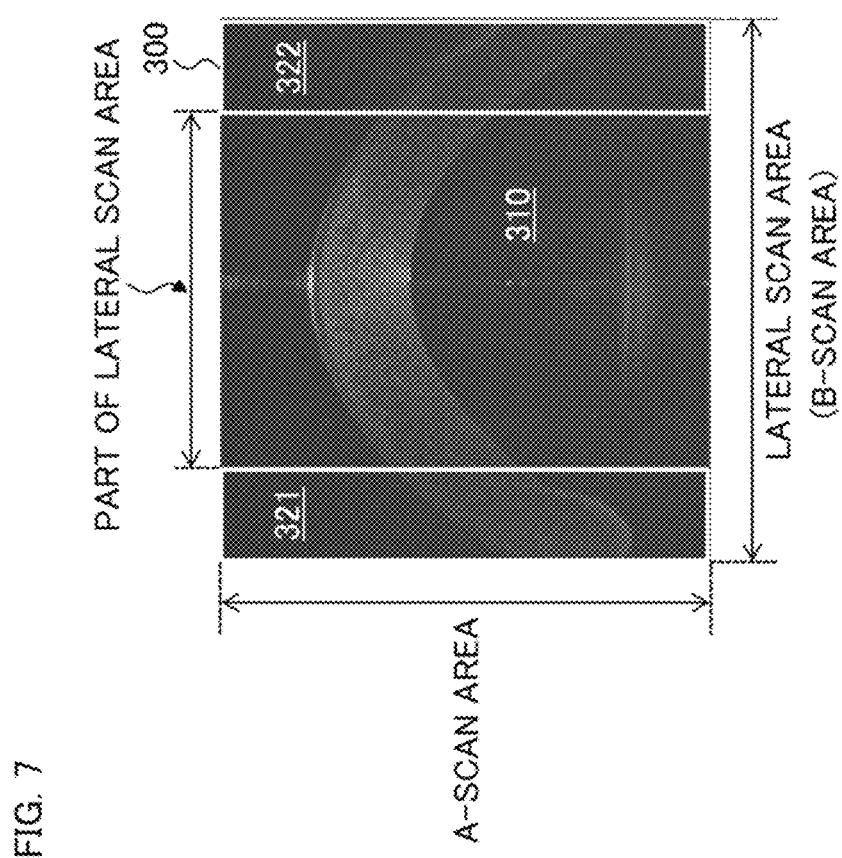
FIG. 7 is a diagram illustrating an example of a process executed by an ophthalmic apparatus according to an aspect example.

The part setting processor 231 of some examples may set the first part 310 shown in FIG. 7 from the anterior segment image 300 (B-scan image) shown in FIG. 6. The first part 310 corresponds to the region (area) obtained by removing the left edge part 321 and the right edge part 322 from the anterior segment image 300. The left edge part 321 is a partial region of the anterior segment image 300 that consists of the group of pixels located within a predetermined distance away from the left edge (left side) of the image frame of the anterior segment image 300, and the right edge part 322 is a partial region of the anterior segment image 300 that consists of the group of pixels located within a predetermined distance away from the right edge (right side) of the image frame of the anterior segment image 300. In this way, the first part 310 is a partial region of the anterior segment image 300 that is defined by the entire A-scan area and by a part of the B-scan area (a part of the lateral scan area). In other words, the first part 310 is the region defined by the upper and lower edges (upper and lower sides) of the image frame of the anterior segment image 300, the right edge (right side) of the left edge part 321, and the left edge (left side) of the right edge part 322. In some aspect examples, the first part may be a partial region of an anterior segment image that is defined by a part of an A-scan area and a part of a B-scan area (a part of a lateral scan area).

The size of both side regions (removed regions) that are removed from an anterior segment image in order to set the first part, may be determined in advance (default value) or may be determined on the basis of this anterior segment image. In some examples, the size of removed regions may be determined based on a normal (usual, standard, ordinary) aspect of depiction of a site of an eye to be identified by the first image region identifying processor 232, a normal aspect of depiction of anterior segment images, or the like.

A specific example will now be described. Suppose that a B-scan is applied to an anterior segment in such a manner that the corneal apex is located at substantially the frame center. By taking account of an empirical fact that the possibility of artifact contamination, such as contamination of an imaginary iris image or an eyelash image, becomes low in the case in which the length of a B-scan is approximately equal to 6 mm or less, the size of removed regions may be determined in such a manner that the size of the first part in the B-scan direction becomes equal to 6 mm. For example, the length of the B-scan of the anterior segment image 300 of FIG. 7 is 9 mm, the left edge part 321 is an image region consisting of pixels located within the distance of 1.5 mm away from the left edge of the image frame, and the right edge part 322 is an image region consisting of pixels located within the distance of 1.5 mm away from the right edge of the image frame. With this, the region between the left edge part 321 and the right edge part 322 is extracted as the first part 310. The length, in the B-scan direction, of the first part 310 defined in this manner is 6 mm.

Note that the size of a left edge part and the size of a right edge part may be the same as each other, or may be different from each other. Further, the shape of a left edge part and the shape of a right edge part are not limited to rectangular shapes as shown in FIG. 7, and may be freely determined. In addition, in the case in which the first part is determined by removing one or more parts of an A-scan area, the size and/or the shape of a removed part(s) of the A-scan area may be determined in the same manner as the size and/or the shape of a B-scan area (lateral scan area).

Described below are several aspect examples of the process of setting the first part. In the first example of the process, the first part of an anterior segment image is determined by referring to a feature point of an anterior segment. The part setting processor 231 of the present example is configured to execute the process of detecting a feature point by analyzing an anterior segment image, and the process of determining the first part of this anterior segment image based on the feature point detected.

The feature point detection may be implemented by using freely selected known image processing techniques and/or freely selected known machine learning techniques. The part setting processor 231 of an example may be configured to detect a feature point by applying edge detection to the entirety of an anterior segment image. The edge detection of some examples is designed to identify (detect) an image corresponding to the anterior surface of the cornea (anterior corneal surface) from the anterior segment image. The image corresponding to the anterior corneal surface is referred to as an anterior corneal surface image. The part setting processor 231 of the present example may identify (detect) the position corresponding to the corneal apex from the anterior corneal surface image detected. The position corresponding to the corneal apex is referred to as a corneal apex position. In the present example, the corneal apex position is used as the feature point.

The setting of the first part on the basis of a feature point may be performed by using the feature point as a reference. The part setting processor 231 of an example may be configured to determine the first part based on the distance from the feature point. In the example in which a corneal apex position is identified as a feature point, the part setting processor 231 may set the first part by determining the region consisting of the group of pixels located within a predetermined distance away from the corneal apex position in the B-scan direction. This predetermined distance is, for example, 3 mm. With this, the area with the B-scan length of 6 mm centered at the corneal apex position in the B-scan direction is designated as the first part.

The present example is capable of setting the first part in such a manner as not to include artifact even in the case in which a corneal apex position is not located at or near the center of an image frame. This makes it possible to set an appropriate first part even in the case in which OCT scanning has been performed with a problem such as with some misalignment.

Note that while the present example is designed to set the first part in such a manner as to include a feature point, some aspect examples are not limited to do so. For example, in the case in which a target of diagnosis (target of observation, target of analysis) is an iris and a feature point is the center of a pupil (pupil center), the region consisting of the group of pixels located at least a predetermined distance away from the pupillary margin (the edge of the pupil) in the B-scan direction may be set to the first part. This predetermined distance is, for example, a standard value of pupil radius.

The second example of the process of setting the first part will now be described. The present example is designed to determine the first part by referring to an artifact in an anterior segment image. The part setting processor 231 of the present example is configured to execute the process of detecting an artifact in an anterior segment image, and the process of determining the first part of the anterior segment image based on the artifact detected.

The artifact detection may be implemented by using freely selected known image processing techniques and/or freely selected known machine learning techniques. The part setting processor 231 of an example may be configured to execute the following processes: the process of partitioning an anterior segment image into multiple partial images; the process of assessing the image quality of each partial image; and the process of finding an artifact by finding a partial image with an image assessment value smaller than a predetermined value.

In another example, the part setting processor 231 may be configured to detect an artifact on the basis of the shape of a predetermined image object in an anterior segment image. For example, taking account of the fact that the shape of a cornea (the shapes of anterior and posterior corneal surfaces) is approximately symmetrical with respect to a straight line passing through the corneal apex (the straight line that passes through the corneal apex and extends in the depth direction), the part setting processor 231 may be configured to detect an artifact by finding a part of an anterior corneal surface image where the symmetry is (greatly, significantly) lost (broken).

In the case in which setting of the first part is performed on the basis of an artifact, the part setting processor 231 may be configured to set the first part in such a manner that the first part does not contain a detected artifact. This makes it possible to provide the first part of high image quality without an artifact to the first image region identifying processor 232.

The part setting processor 231 is implemented by cooperation between hardware including the one or more processors and part setting software.

<First Image Region Identifying Processor 232>

The first image region identifying processor 232 is configured to perform identification of an image region corresponding to a predetermined part (site, tissue) of the anterior segment Ea by analyzing the first part of the anterior segment image set by the part setting processor 231. The image region identified from the first part by the first image region identifying processor 232 is referred to as the first image region.

In some aspect examples, the part of the anterior segment Ea to be detected as the first image region from the first part of an anterior segment image may be determined in advance. Examples of the part of the anterior segment Ea to be detected include a cornea, an iris, an anterior chamber, a pupil, a crystalline lens, and other parts. Note that the part of the anterior segment Ea to be detected may include a part of any of a cornea, an iris, an anterior chamber, a pupil, a crystalline lens, and other parts. Also note that the part of the anterior segment Ea to be detected may include a combination of at least parts of two or more of a cornea, an iris, an anterior chamber, a pupil, a crystalline lens, and other parts.

The first image region identifying processor 232 of some examples may be configured to execute the identification of the first image region by applying segmentation to the first part of an anterior segment image. This segmentation is executed in such a manner as to, for example, identify a region in the first part that corresponds to a predetermined part of an anterior segment. This segmentation may be implemented by using any known image processing techniques. In some examples, this segmentation may include a freely selected image processing such as edge detection, and/or, a freely selected machine learning based segmentation.

In some aspect examples, the first image region identifying processor 232 may be configured to identify the first image region that corresponds to the cornea of the anterior segment Ea or a part of the cornea, by analyzing the first part of the anterior segment image. For example, the first image region identifying processor 232 of the present example may be configured to identify both the first image region corresponding to the anterior surface of the cornea and the first image region corresponding to the posterior surface of the cornea, by analyzing the first part of the anterior segment image. Here, the first image region corresponding to the anterior corneal surface is referred to as the first anterior corneal surface image, and the first image region corresponding to the posterior corneal surface is referred to as the first posterior corneal surface image.

Several examples will now be described of the first image region identifying processor 232 that is configured to apply edge detection in order to identify the first image region, especially, in order to identify the first anterior corneal surface image and the first posterior corneal surface image.

In some aspect examples, in order to identify the first anterior corneal surface image, the first image region identifying processor 232 may be configured to executed the process of detecting an edge where the gradient direction is toward a frame edge of an anterior segment image and where the gradient value (gradient intensity, gradient strength, gradient magnitude) is equal to or greater than a predetermined threshold value.

Also, in some aspect examples, in order to identify the first posterior corneal surface image, the first image region identifying processor 232 may be configured to executed the process of detecting an edge where the gradient direction is toward a central region of the frame of an anterior segment image and where the gradient value is equal to or greater than a predetermined threshold value.

The edge detection technique on the basis of a gradient (gradient direction, gradient intensity) described above can be applied to the case in which the first image region corresponding to other parts of an anterior segment is to be identified. Note that, in typical examples, a gradient direction may be defined to be the direction of a normal (normal line, normal vector) to that gradient.

The edge detection for the identification of the first anterior corneal surface image will now be described in more detail with referring to FIG. 8A and FIG. 8B. The present example is designed to identify the first anterior corneal surface image 311 from the first part 310 of FIG. 7. As described above, the first image region identifying processor 232 of the present example is configured to identify the first anterior corneal surface image by detecting an edge where the gradient direction is toward a frame edge of an anterior segment image and where the gradient value is equal to or greater than a predetermined threshold value. The present example describes the case in which the first image region identifying processor 232 analyzes the one dimensional region 312 shown in FIG. 8A. The one dimensional region 312 consists of an array of multiple pixels (see also FIG. 8B). The reference character 313 in FIG. 8B indicates a brightness distribution graph for the plurality of pixels arranged in the one dimensional region 312. As can be seen from the shape of the brightness distribution graph 313, a portion of the brightness distribution graph 313 meets the following conditions: a condition that the gradient value of brightness is greater than the predetermined threshold value 314; and a condition that the normal direction (normal vector) 313a that indicates the direction of the gradient is toward the left edge 310L of the frame (left frame edge 310L) of the first part 310. A region with such gradients is detected as an edge. By applying such processing to various one dimensional regions, the first anterior corneal surface image 311 can be identified.

Figure 8A:
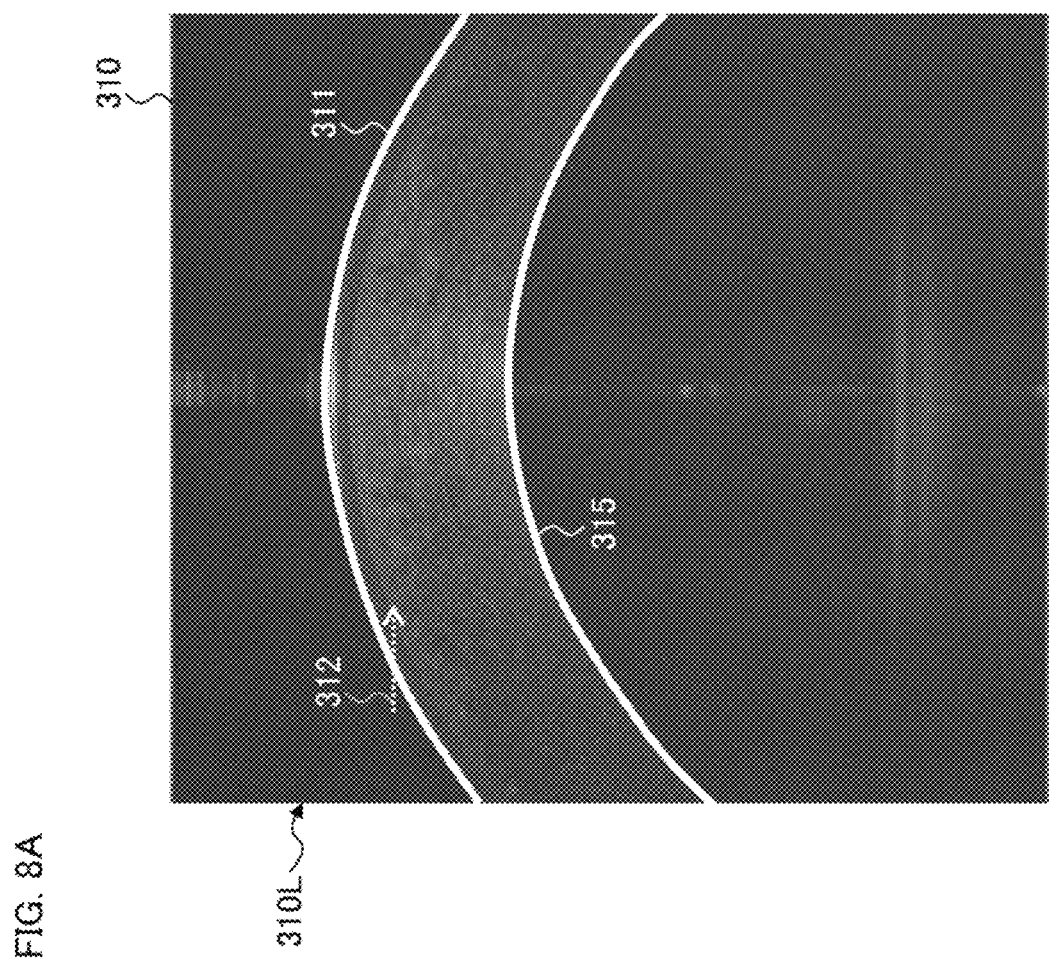
FIG. 8A is a diagram illustrating an example of a process executed by an ophthalmic apparatus according to an aspect example.

Note that, in FIG. 8A, a pixel on the one dimensional image 312 corresponding to the first anterior corneal surface image 311 is located to the left of the corneal apex, and the normal direction 313a at this pixel is toward the left frame edge 310L. Although not shown in the diagrams, in the case in which a pixel on a one dimensional image corresponding to the first anterior corneal surface image 311 is located to the right of the corneal apex, the normal direction at this pixel is toward the right edge of the frame (right frame edge) of the first part 310. Taking this into account, the first anterior corneal surface image can be identified by detecting an edge where the normal direction is toward the right frame edge and where the gradient value is equal to or greater than a predetermined threshold value.

Similarly, the first image region identifying processor 232 can identify the first posterior corneal surface image 315 shown in FIG. 8A by detecting an edge where the gradient direction is toward a central region of the frame of an anterior segment image and where the gradient value is equal to or greater than a predetermined threshold value.

The first image region identifying processor 232 is implemented by cooperation between hardware including the one or more processors and first image region identifying software.

<Second Image Region Identifying Processor 233>

The second image region identifying processor 233 is configured to perform, based on the first image region, which corresponds to a predetermined part of the anterior segment Ea, identified by the first image region identifying processor 232, identification of the second image region corresponding to this predetermined part. Here, the second image region is inside the second part, and the first part identified from the anterior segment image by the part setting processor 231 is a proper subset of the second part.

For example, the second image region identifying processor 233 may be configured to identify, based on the first anterior corneal surface image 311 identified from the first part 310 of the anterior segment image 300 by the first image region identifying processor 232, the second anterior corneal surface image corresponding to the anterior corneal surface in the second part that includes the first part 310 as a proper subset. In addition, the second image region identifying processor 233 may be configured to identify, based on the first posterior corneal surface image 315 identified from the first part 310 of the anterior segment image 300 by the first image region identifying processor 232, the second posterior corneal surface image corresponding to the posterior corneal surface in the second part that includes the first part 310 as a proper subset.

In the present aspect example, the second part contains not only the first part but also a part other than the first part. In other words, the second part includes the first part and the size (e.g., the area or the volume) of the second part is greater than the size of the first part. Note that the first part is a proper subset of an anterior segment image, that is, the first part is not the entirety of the anterior segment image. On the other hand, the second part may be either a proper subset of the anterior segment image or the entirety of the anterior segment image, following the definition of a subset in set theory.

The size of the second part may be determined in advance or may be determined for each process. The size of the second part may be determined on the basis of the size of the first part. In some examples, the relationship (e.g., difference, ratio, etc.) between the size of the first part and the size of the second part is determined in advance, and the second part is formed by enlarging (widening, expanding, broadening) the first part based on this relationship. Further, the shape of the second part may be determined in advance or may be determined for each process.

In some typical examples, the second part is the entirety of an anterior segment image. In a specific example, an anterior segment image is a relatively wide angle image (e.g., B-scan image with the length of 9 mm, 12 mm, or 16 mm), a proper subset of this anterior segment image is set to the first part, and the entirety of this anterior segment image is set to the second part. This specific example makes it possible to apply identification of an image of a predetermined part of an anterior segment (identification of the second image region) to the entirety of a relatively wide angle image that is comparatively easily contaminated by an artifact.

The process of determining the second image region from the first image region executed by the second image region identifying processor 233, may be implemented by using any known image processing techniques. In some examples, this process may include a freely selected image processing, and/or, a freely selected machine learning based segmentation. This image processing for enlarging the first image region to the second image region may include, for example, any one or more of curve fitting, edge detection, and region growing.

Figure 9:
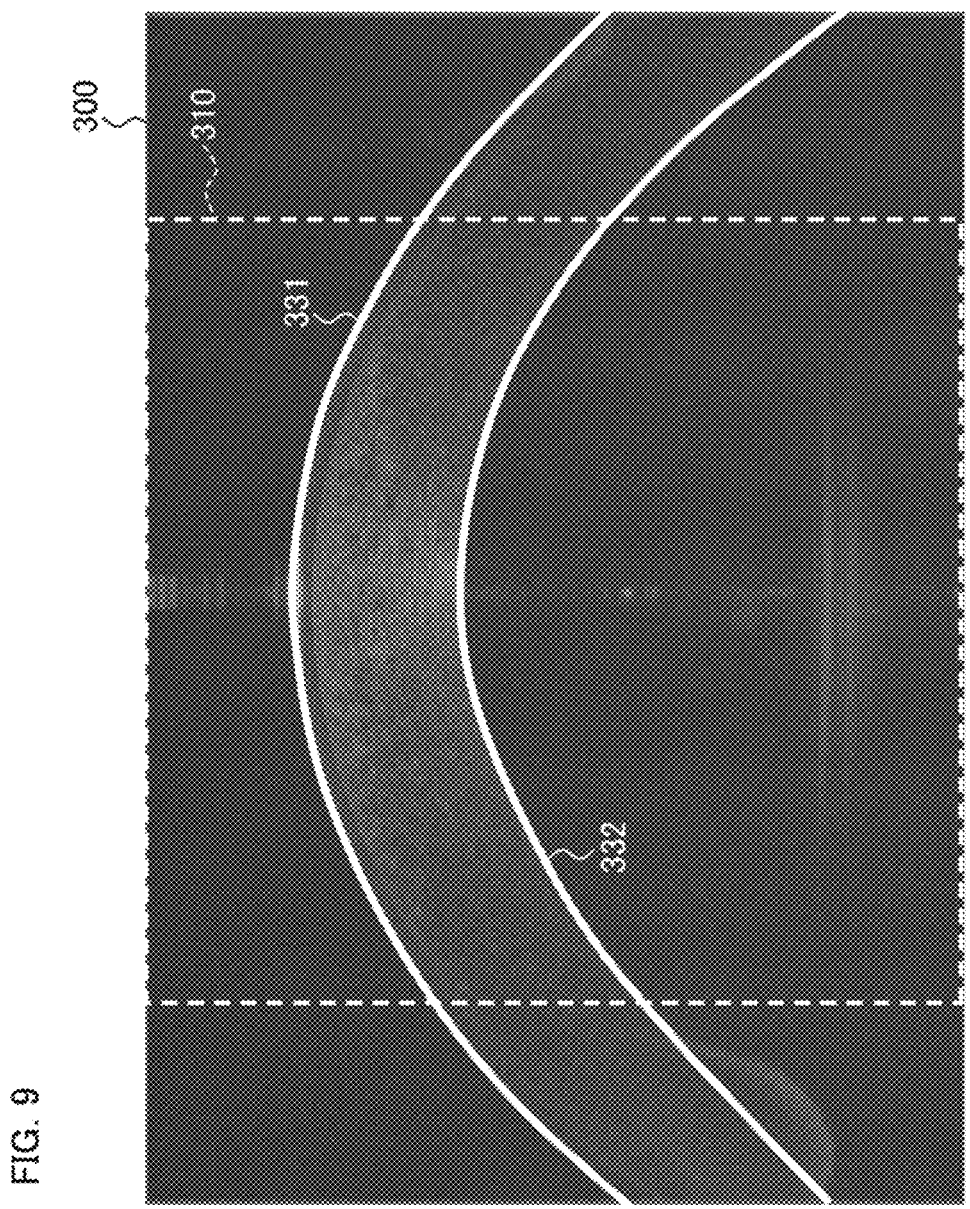
FIG. 9 is a diagram illustrating an example of a process executed by an ophthalmic apparatus according to an aspect example.

An example will now be described in which curve fitting is applied to the first anterior corneal surface image 311 in the first part 310 of the anterior segment image 300 (FIG. 8A). In the present example, the second image region identifying processor 233 applies curve fitting to the first anterior corneal surface image 311 to derive an approximate curve corresponding to the anterior corneal surface in (the entirety of) the anterior segment image 300. This approximate curve is used as the second anterior corneal surface image. In other words, the second image region identifying processor 233 of the present example is configured to perform estimation of the shape of the anterior corneal surface over the entirety of the anterior segment image 300 based on the first anterior corneal surface image 311 identified from the first part 310. The estimated shape of the anterior corneal surface is used as the second anterior corneal surface image. With this configuration, for example, as shown in FIG. 9, the approximate curve 331 (the second anterior corneal surface image) representing an estimated shape of the anterior corneal surface over the entirety of the anterior segment image 300, is determined. An approximate curve of the present example may be of any aspect (any definition), and may be a quartic curve (a curve of the fourth degree).

The second image region identifying processor 233 may be configured to apply, to the first anterior corneal surface image 311, curve fitting on the basis of a robust estimation algorithm for removing an outlier. This robust estimation algorithm may include a random sample consensus (RANSAC) algorithm. By employing such a robust estimation algorithm, it becomes possible to remove an outlier(s) caused by noise or other factors, thereby performing curve fitting with a high degree of accuracy on the first anterior corneal surface image 311. This makes it possible to obtain the second anterior corneal surface image 331 that is a good approximation of the anterior corneal surface.

Further, the second image region identifying processor 233 of the present example applies curve fitting to the first posterior corneal surface image 315 to derive an approximate curve corresponding to the posterior corneal surface in (the entirety of) the anterior segment image 300. This approximate curve is used as the second posterior corneal surface image. In other words, the second image region identifying processor 233 of the present example is configured to perform estimation of the shape of the posterior corneal surface over the entirety of the anterior segment image 300 based on the first posterior corneal surface image 315 identified from the first part 310. The estimated shape of the posterior corneal surface is used as the second posterior corneal surface image. With this configuration, for example, as shown in FIG. 9, the approximate curve 332 (the second posterior corneal surface image) representing an estimated shape of the posterior corneal surface over the entirety of the anterior segment image 300, is determined. An approximate curve of the present example may be of any aspect (any definition), and may be a quartic curve. The second image region identifying processor 233 may be configured to apply, to the first posterior corneal surface image 315, curve fitting on the basis of a robust estimation algorithm for removing an outlier, and more specifically, curve fitting on the basis of a RANSAC algorithm, for example. By employing such a robust estimation algorithm, it becomes possible to remove an outlier(s) caused by noise or other factors, thereby performing curve fitting with a high degree of accuracy on the first posterior corneal surface image 315. This makes it possible to obtain the second posterior corneal surface image 332 that is a good approximation of the posterior corneal surface.

The second image region identifying processor 233 is implemented by cooperation between hardware including the one or more processors and second image region identifying software.

<Analysis Region Setting Processor 234>

The analysis region setting processor 234 is configured to perform setting of an analysis region that includes the second image region identified by the second image region identifying processor 233. The analysis region is used in an analysis process executed by the third image region identifying processor 235, and the setting of the analysis region corresponds to masking processing (image masking) as a preparation for this analysis process executed by the third image region identifying processor 235. Thus, the aspect of the analysis region is determined mainly in keeping with the aspect of this analysis process.

In the case in which the second image region is a linear-shaped region such as the second anterior corneal surface image 331 or the second posterior corneal surface image 332, the analysis region setting processor 234 may set a region consisting of this linear-shaped region and a neighborhood region (vicinity region, adjacent region, surrounding region, etc.) of this linear-shaped region, to an analysis region.

The analysis region setting processor 234 of some examples may be configured to set an analysis region by increasing the width of the second image region identified by the second image region identifying processor 233 to a predetermined value. This predetermined value (that is, the width of the analysis region) may or may not be uniform (constant, the same) in the entirety of the analysis region.

Figure 10:
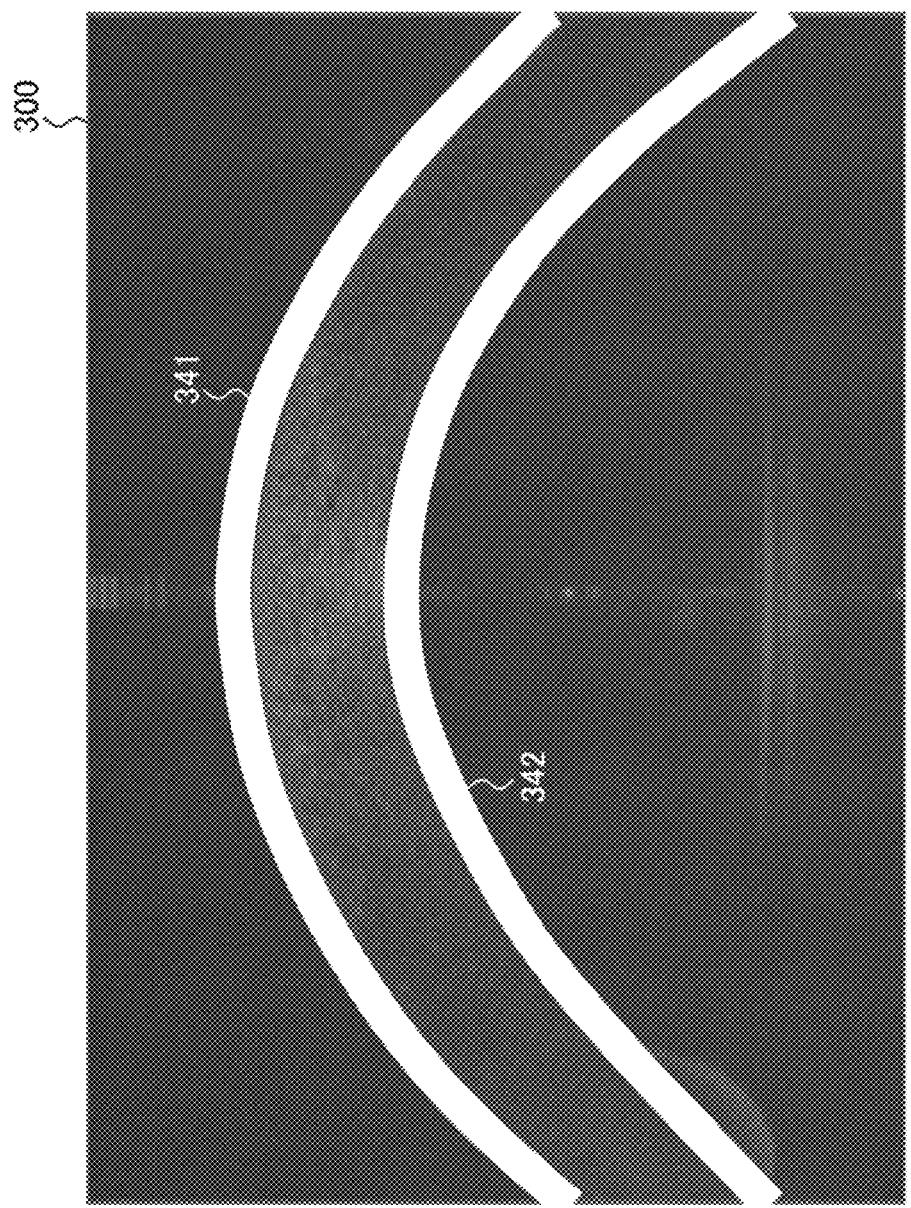
FIG. 10 is a diagram illustrating an example of a process executed by an ophthalmic apparatus according to an aspect example.

In some specific examples, the analysis region setting processor 234 may increase the width of the second anterior corneal surface image 331 shown in FIG. 9 to a predetermined value, thereby setting the analysis region (anterior surface analysis region) 341 shown in FIG. 10. The anterior surface analysis region 341 includes the second anterior corneal surface image 331. Further, the analysis region setting processor 234 may increase the width of the second posterior corneal surface image 332 shown in FIG. 9 to a predetermined value, thereby setting the analysis region (posterior surface analysis region) 342 shown in FIG. 10. The posterior surface analysis region 342 includes the second posterior corneal surface image 332. The width of the anterior surface analysis region 341 and the width of the posterior surface analysis region 342 may be equal to each other or may be different from each other.

In some examples, the width of a linear-shaped region may be defined in the direction perpendicular to the tangent line at a given point on the linear-shaped region. Similarly, in some examples, the width of the second image region that is a belt-shaped region may be defined in the direction perpendicular to the tangent line at a given point on an axis image of the belt-shaped region. Note that an axis image is a linear-shaped image formed by applying thinning (skeletonization) to a belt-shaped region.

The width (the predetermined value mentioned above) of an analysis region may be determined in advance or may be determined for each process. In some examples of the former case, the width of an analysis region may be determined in advance based on a standard distribution of artifacts occurred around an image of a predetermined part of an anterior segment (e.g., cornea, anterior corneal surface, posterior corneal surface) in an anterior segment image. In some examples of the latter case, the width of an analysis region may be determined by detecting artifacts around an image of a predetermined part of an anterior segment in an anterior segment image and by determining the width of an analysis region based on a distribution of the detected artifacts.

The analysis region setting processor 234 is implemented by cooperation between hardware including the one or more processors and analysis region setting software.

<Third Image Region Identifying Processor 235>

The image region identifying processor 235 is configured to perform identification of the third image region corresponding to the predetermined part of the anterior segment by analyzing the analysis region set by the analysis region setting processor 234. Here, the predetermined part of the anterior segment is the same as the part corresponding to the first image region and the second image region. The method of analysis used for the identification of the third image region may be the same as or different from the method of analysis used for the identification of the first image region.

Figure 11:
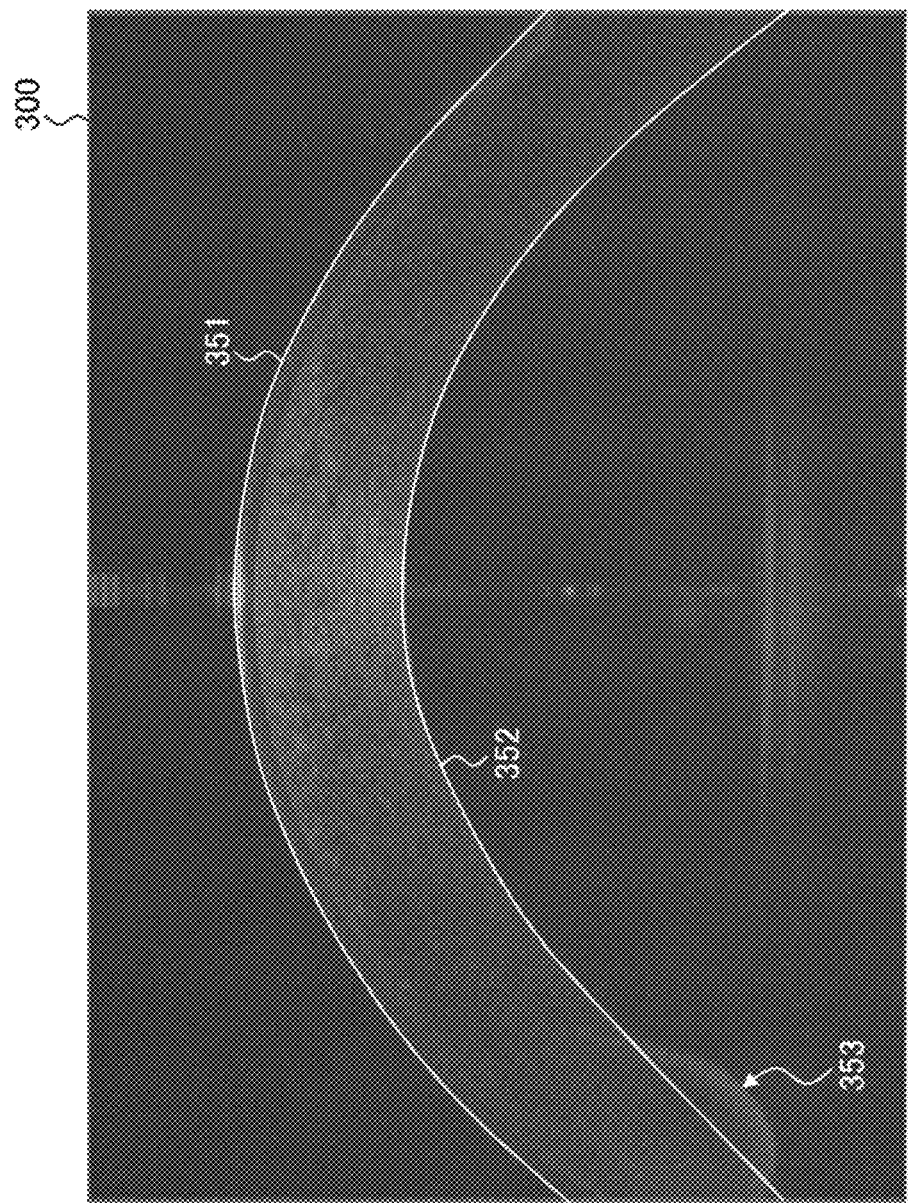
FIG. 11 is a diagram illustrating an example of a process executed by an ophthalmic apparatus according to an aspect example.

For example, the third image region identifying processor 235 may analyze the anterior surface analysis region 341 shown in FIG. 10, thereby identifying the third anterior corneal surface image 351 shown in FIG. 11 as the third image region corresponding to the anterior corneal surface. Further, the third image region identifying processor 235 may analyze the posterior surface analysis region 342 shown in FIG. 10, thereby identifying the third posterior corneal surface image 352 shown in FIG. 11 as the third image region corresponding to the posterior corneal surface. In the anterior segment image 300 of FIG. 11, the imaginary image (virtual image, inverted image, folded image) 353 of the iris overlaps the image of the cornea (especially, the edge part of the posterior corneal surface); however, the third posterior corneal surface image 352 has been determined without the influence of the imaginary image 353.

In some aspect examples, both of the methods of analysis may be edge detection. If this is the case, a threshold value of a gradient value used in the edge detection performed by the third image region identifying processor 235 may be smaller than a threshold value of a gradient value used in the edge detection performed by the first image region identifying processor 232. In other words, the third image region identifying processor 235 may be configured to detect, as an edge, a location where a gradient value is smaller than a gradient value that can be detected as an edge by the first image region identifying processor 232. An edge that exists in an area with an overlapping artifact, is more unclear (more indistinct, vaguer) than an edge that exists in an area with no artifact. Therefore, the reliability of detection of an unclear edge (the sensitivity of edge detection) can be improved by setting a comparatively (relatively) small threshold value of a gradient value used in the edge detection performed by the third image region identifying processor 235.

The third image region identifying processor 235 is implemented by cooperation between hardware including the one or more processors and third image region identifying software.

<Distortion Correcting Processor 236>

The distortion correcting processor 236 is configured to perform correction of distortion of the anterior segment image based on the third image region identified by the third image region identifying processor 235. In the present example, the distortion correcting processor 236 may be configured to correct the distortion of the anterior segment image 300 based at least on the third anterior corneal surface image 351 shown in FIG. 11. The image distortion correction of the present example is an image correction technique on the basis of the influence of refraction at the anterior surface of the cornea (refraction correction).

Figure 12:
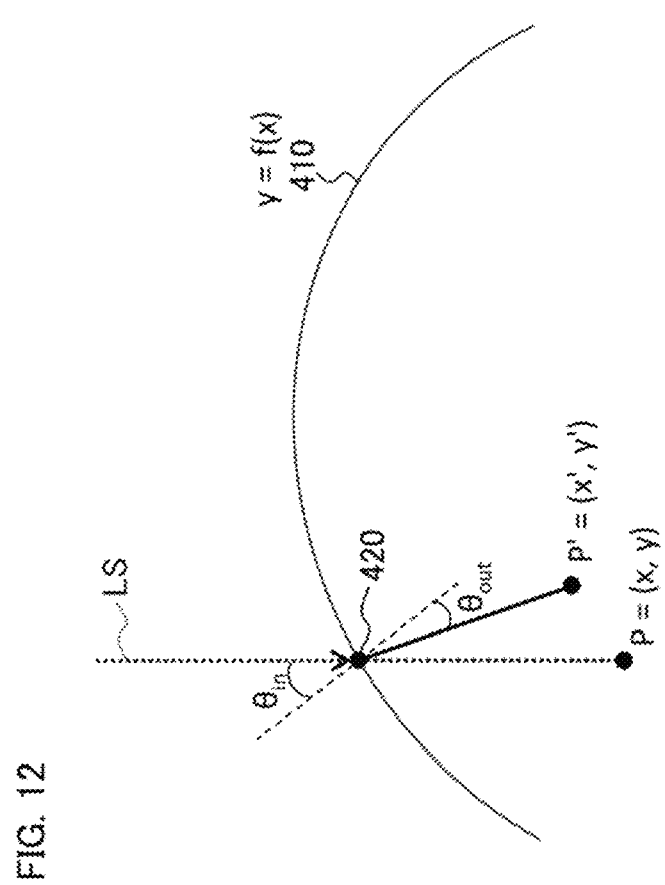
FIG. 12 is a diagram illustrating an example of a process executed by an ophthalmic apparatus according to an aspect example.

An example of the refraction correction will now be described with referring to FIG. 12. Let $y=f(x)$ be the equation (mathematical expression) expressing the anterior corneal surface 410 (the third anterior corneal surface image 351, or an approximate curve of the third anterior corneal surface image 351). In addition, suppose that the value of the refractive index of air (e.g., 1.000292) and the value of the refractive index of the cornea (e.g., 1.376) are set.

The light beam (the measurement light LS) incident onto the point 420 on the anterior corneal surface 410 is now considered. Let $\theta_{in}$ be the angle of incidence of the measurement light LS at the point 420. Then, the angle of refraction $\theta_{out}$ of the measurement light LS is derived from the angle of incidence $\theta_{in}$, the refractive index of air, and the refractive index of the cornea by Snell's law.

In addition, let $r_{air}$ be the distance per pixel (resolution) in air, let $r_{cor}$ be the distance per pixel (resolution) in cornea, and let $r_h$ be the quotient (ratio) of the length of a scan (e.g., 16 mm) over the number of pixels (e.g., 1024). Then, the function $T=|f(x)-y|$ is considered.

Now, consider the point (pixel) $P=(x, y)$ located at a position below the anterior corneal surface 410 in the anterior segment image 300 before distortion correction. That is, consider the point (pixel) $P=(x, y)$ located at a position between the anterior corneal surface 410 and the lower edge of the frame in the anterior segment image 300 before distortion correction. Then, the point $P'=(x', y')$ derived by applying refraction correction to the point $P=(x, y)$ is expressed by the following equations: $x'=T(r_{cor}/r_h)*\sin(\theta_{in}-\theta_{out})$, $y'=T(r_{cor}/r_{air})*\cos(\theta_{in}-\theta_{out})$.

By applying such refraction correction to each point (each pixel) located below the anterior corneal surface 410 in the anterior segment image 300 before distortion correction, the distortion of the anterior segment image 300 caused by refraction at the anterior corneal surface can be corrected. Note that the vertical resolutions (resolutions in the vertical direction, resolutions in the upward and downward direction of the frame) at the individual coordinates (x', y') after the refraction correction are uniformly the resolution in air "$r_{air}$".

The distortion correcting processor 236 is implemented by cooperation between hardware including the one or more processors and distortion correcting software.

<Aspect Ratio Correcting Processor 237>

The aspect ratio correcting processor 237 is configured to perform correction of the pixel aspect ratio of an anterior segment image of the subject's eye E. The image data constructing unit 220 constructs an OCT image (anterior segment image, fundus image) of a predetermined pixel aspect ratio, from data acquired by OCT scanning.

Figure 13:
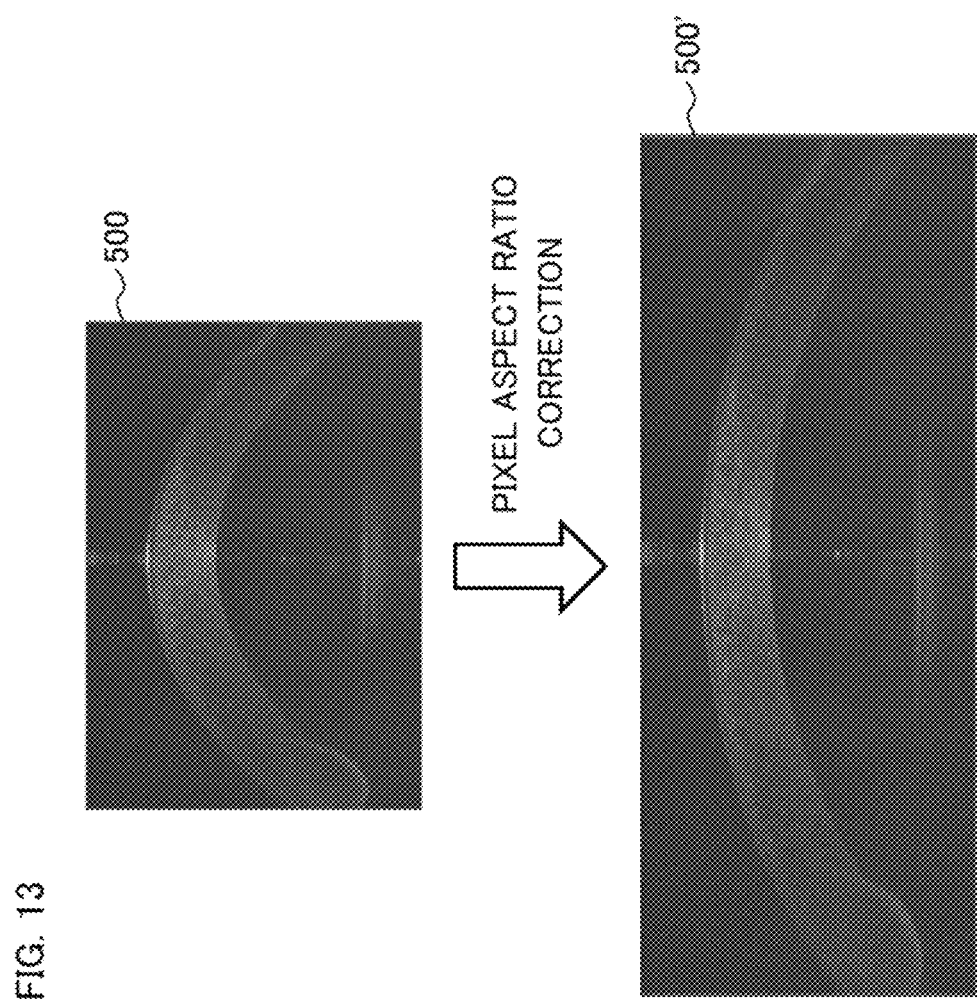
FIG. 13 is a diagram illustrating an example of a process executed by an ophthalmic apparatus according to an aspect example.

The aspect ratio correcting processor 237 of some typical examples is configured to convert (transform) this OCT image into an image of the pixel aspect ratio corresponding to the real space, that is, an image of the pixel aspect ratio 1:1. With this pixel aspect ratio correction, for example, as shown in FIG. 13, the anterior segment image 500 of a predetermined pixel aspect ratio constructed by the image data constructing unit 220 is converted into the anterior segment image 500' of the pixel aspect ratio 1:1.

Execution of the pixel aspect ratio correction allows an anterior segment image that represents the actual morphology of an anterior segment to be obtained. In addition, analysis of this anterior segment image can generate analysis data that reflects the real states (real conditions) of the anterior segment such as the real scale, the real size, and the real shape of the anterior segment. Here, examples of the analysis data may include any kinds of distribution data such as corneal thickness distribution, any kinds of an anterior segment parameter such as a corner angle parameter.

The aspect ratio correcting processor 237 of the present example is configured to correct the pixel aspect ratio of an anterior segment image whose distortion has already been corrected by the distortion correcting processor 236. In other words, the ophthalmic apparatus 1 of the present example is configured to perform pixel aspect ratio correction after image distortion correction. However, in aspect examples, the stage in which and the timing at which pixel aspect ratio correction is performed may be freely selected. In some aspect examples, the timing of execution of pixel aspect ratio correction may be any of the following time points: a time point after the process of constructing an OCT image, a time point prior to the process of setting a part of an anterior segment; a time point after the process of setting the part; a time point prior to the process of identifying the first image region; a time point after the process of identifying the first image region; a time point prior to the process of identifying the second image region; a time point after the process of identifying the second image region; a time point prior to the process of setting an analysis region; a time point after the process of setting an analysis region; a time point prior to the process of identifying the third image region; a time point after the process of identifying the third image region; a time point prior to the process of correcting image distortion; and a time point after the process of correcting image distortion.

Some aspect examples may be configured to apply correction processing equivalent to pixel aspect ratio correction, to analysis data derived by the analyzing processor 238.

The aspect ratio correcting processor 237 is implemented by cooperation between hardware including one or more processors and pixel aspect ratio correcting software.

<Analyzing Processor 238>

The analyzing processor 238 is configured to perform calculation of a predetermined anterior segment parameter by analyzing an anterior segment image of the subject's eye E.

The analyzing processor 238 of some aspect examples may be configured to perform calculation of a predetermined anterior segment parameter by analyzing an anterior segment image to which at least distortion correction has already been applied. With this configuration, it becomes possible to execute anterior segment parameter calculation with a high degree of accuracy and a high degree of precision based on an anterior segment image with distortion corrected.

Further, as shown in the example of FIG. 5, the analyzing processor 238 of some aspect examples may be configured to perform calculation of a predetermined anterior segment parameter by analyzing an anterior segment image to which both distortion correction and pixel aspect ratio correction have already been applied. With this configuration, it becomes possible to execute anterior segment parameter calculation with even higher degree of accuracy and even higher degree of precision based on an anterior segment image with distortion and pixel aspect ratio both corrected. Note that in the present example, pixel aspect ratio correction is performed after image distortion correction and anterior segment analysis is performed after the pixel aspect ratio correction.

The anterior segment parameter(s) calculated by the analyzing processor 238 may be freely selected. An anterior segment parameter is a value representing the morphology (shape, form) of an anterior segment. Examples of anterior eye parameters include corneal thickness (central thickness, peripheral thickness), corner angle parameters, radius of curvature of anterior corneal surface, radius of curvature of posterior corneal surface, radius of curvature of anterior surface of crystalline lens, radius of curvature of posterior surface of crystalline lens, corneal diameter (vertical diameter, horizontal diameter (white-to-white)), crystalline lens thickness, anterior chamber depth, anterior chamber volume, pupil diameter, and pupil center (eccentricity). The anterior segment parameter(s) may include distribution data, and may include, for example, one or more of a curvature map in the axial direction (axial curvature map), a tangential curvature map, an elevation map, a refractive power map, a thickness map (pachymetry map), and a wavefront aberration map.

The methods and techniques of anterior segment parameter calculation may be freely selected (see, for example, PATENT DOCUMENTS 1 to 4). In some typical examples, anterior segment parameter calculation may include a process of identifying a predetermined part of an anterior segment (e.g., a process of segmentation, a process of feature point detection), and a measurement process such as any of distance measurement, area measurement, volume measurement, ratio calculation, and angle calculation.

In some aspect examples, the analyzing processor 238 may be configured to create a corneal thickness map (corneal pachymetry map). For example, the analyzing processor 238 may obtain corneal thickness distribution data of the subject's eye E on the basis of the third anterior corneal surface image 351 and the third posterior corneal surface image 352 shown in FIG. 11. In order to obtain corneal thickness distribution data, the analyzing processor 238 of some examples may execute the following processes: the process of deriving the tangent line at each of multiple positions on the third anterior corneal surface image 351 (or the third posterior corneal surface image 352); the process of calculating the distance between the third anterior corneal surface image 351 and the third posterior corneal surface image 352 in the direction of the normal (normal line, normal vector) to the tangent line at each position; and the process of creating a map by arranging multiple distance values obtained for the multiple positions in accordance with the disposition of the multiple positions.

The analyzing processor 238 of some aspect examples may be configured to perform calculation of a corner angle parameter. A corner angle parameter is a parameter related to the site called corner angle (also referred to as angle of anterior chamber or anterior chamber angle) located between a cornea and an iris. Trabecular meshwork exists in a corner angle. The magnitude of a corner angle is considered to be one of determining factors of the flow speed of aqueous humor drained from an eyeball, and therefore one of determining factors of intraocular pressure. A corner angle parameter is used as an important index (important indicator, important information) for diagnosis of glaucoma, especially diagnosis of angle closure glaucoma. Examples of corner angle parameters include angle opening distance (AOD), anterior chamber angle (ACA), trabecular iris space area (TISA), angle recess area (ARA), and angle-to-angle distance (AtA) (see, for example, PATENT DOCUMENTS 1 to 3). The methods and techniques of corner angle parameter calculation may be freely selected (see, for example, PATENT DOCUMENTS 1 to 3). In some typical examples, corner angle parameter calculation may include a process of identifying the position of a corner angle or a predetermined position (location) in the vicinity of a corner angle (e.g., a process of segmentation, a process of feature point detection), and a measurement process such as any of distance measurement, ratio calculation, and angle calculation.

The analyzing processor 238 is implemented by cooperation between hardware including one or more processors and analyzing software.

<User Interface 240>

The user interface 240 includes the display device 241 and the operation device 242. The display device 241 includes the display device 3. The operation device 242 includes various operation devices and various input devices. The user interface 240 may include a device that has both a display function and an operation function, such as a touch panel. Some embodiment may not include at least part of the user interface 240. For example, a display device may be an external device or a peripheral device that is connected to the ophthalmic apparatus 1.

<Operation of Ophthalmic Apparatus>

Figure 14:
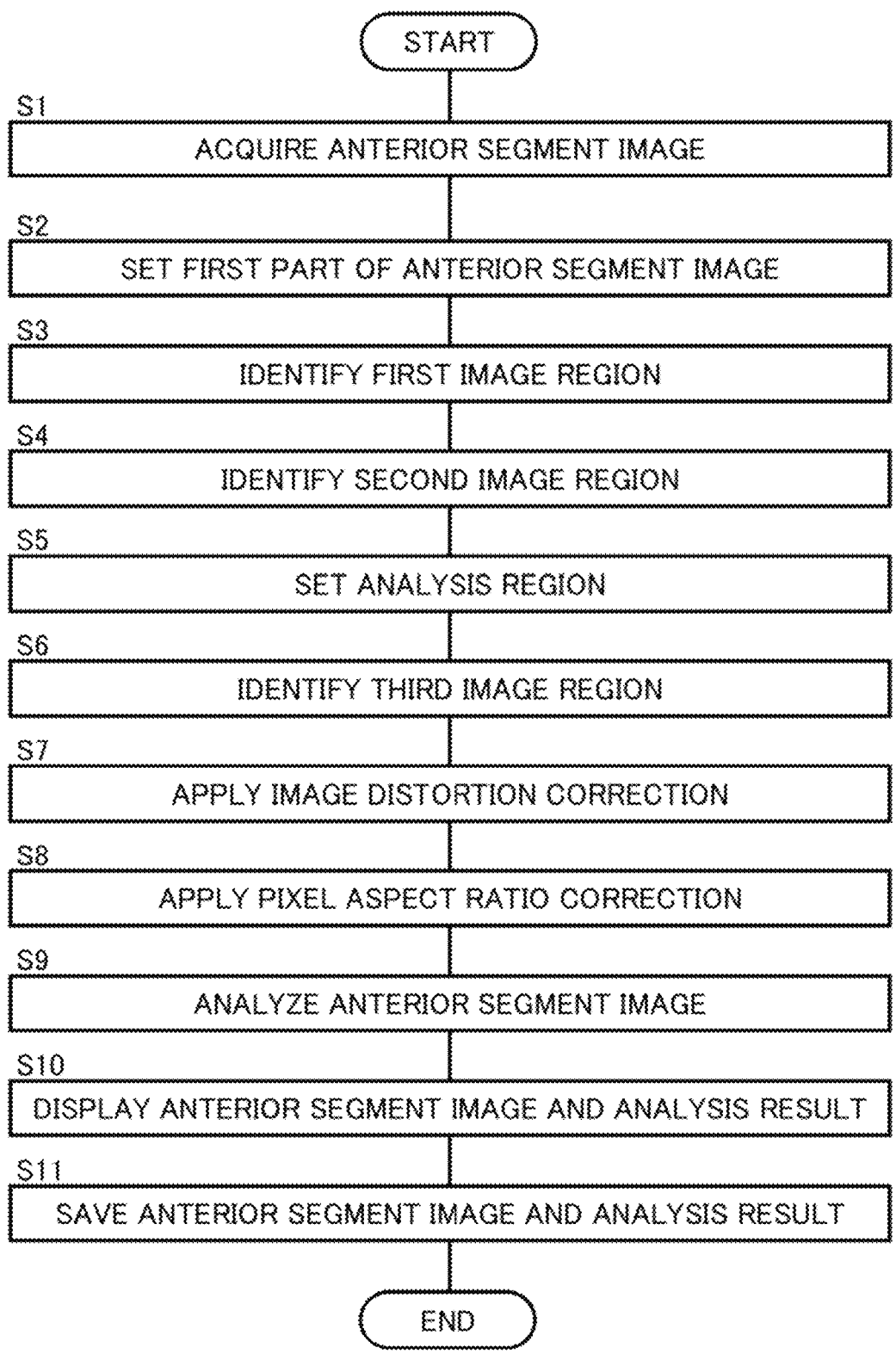
FIG. 14 is a flowchart illustrating an example of an operation executed by an ophthalmic apparatus according to an aspect example.

Several examples of the operation of the ophthalmic apparatus 1 will be described. The same or similar preparatory processes as those performed by existing or conventional ophthalmic apparatuses are performed before the operation described below. Examples of such preparatory processes may include the process of entering a patient identifier (ID), the process of inserting the anterior segment OCT attachment 400 into the sample arm, the process of presenting a fixation target to the subject's eye E, the process of adjusting fixation position, the process of alignment, the process of focus adjustment, and the process of OCT optical path length adjustment. FIG. 14 shows an example of the operation of the ophthalmic apparatus 1.

(S1: Acquire anterior segment image)

To begin with, the ophthalmic apparatus 1 acquires an anterior segment image of the subject's eye E. In the present example, the ophthalmic apparatus 1 collects data from the anterior segment Ea by applying OCT scanning to the anterior segment Ea using the OCT scanner (the sample arm in the fundus camera unit 2, and the OCT unit 100, etc.), and constructs an anterior segment image from the collected data using the image data constructing unit 220. In this way, the present example obtains the anterior segment image 300 shown in FIG. 6. The controller 210 sends the acquired anterior segment image (B-scan image) 300 to the data processor 230. The anterior segment image 300 sent to the data processor 230 is input to the part setting processor 231.

(S2: Set First Part of Anterior Segment Image)

Next, the part setting processor 231 sets the first part of the anterior segment image 300 acquired in the step S1 by setting a part of the anterior segment image 300 defined by at least part of the A-scan area and a part of the B-scan area (lateral scan area). Suppose that the first part 310 shown in FIG. 7 is set for the anterior segment image 300.

(S3: Identify First Image Region)

Next, the first image region identifying processor 232 analyzes the first part 310 of the anterior segment image 300 set in the step S2 to identify the first anterior corneal surface image 311 corresponding to the anterior corneal surface of the subject's eye E and the first posterior corneal surface image 315 corresponding to the posterior corneal surface (see FIG. 8A).

(S4: Identify Second Image Region)

Next, based on the first anterior corneal surface image 311 identified in the step S3, the second image region identifying processor 233 identifies the second anterior corneal surface image 331 corresponding to the anterior corneal surface in the entirety of the anterior segment image 300 (more generally, in the second part that includes the first part 310 as a proper subset) (see FIG. 9). Further, based on the first posterior corneal surface image 315 identified in the step S3, the second image region identifying processor 233 identifies the second posterior corneal surface image 332 corresponding to the posterior corneal surface in the entirety of the anterior segment image 300 (more generally, in the second part that includes the first part 310 as a proper subset) (see FIG. 9).

(S5: Set Analysis Region)

Next, the analysis region setting processor 234 sets the anterior surface analysis region 341 that includes the second anterior corneal surface image 331 identified in the step S4 (see FIG. 10). Further, the analysis region setting processor 234 sets the posterior surface analysis region 342 that includes the second posterior corneal surface image 332 identified in the step S4 (see FIG. 10).

(S6: Identify Third Image Region)

Next, the third image region identifying processor 235 analyzes the anterior surface analysis region 341 set in the step S5 to identify the third anterior corneal surface image 351 corresponding to the anterior corneal surface (see FIG. 11). Further, the third image region identifying processor 235 analyzes the posterior surface analysis region 342 set in the step S5 to identify the third posterior corneal surface image 352 corresponding to the posterior corneal surface (see FIG. 11).

(S7: Apply Image Distortion Correction)

Next, the distortion correcting processor 236 corrects distortion of the anterior segment image 300 based at least on the third anterior corneal surface image 351 obtained in the step S6.

(S8: Apply Pixel Aspect Ratio Correction)

Next, the aspect ratio correcting processor 237 corrects the pixel aspect ratio of the anterior segment image 300 with distortion corrected in the step S7.

(S9: Analyze Anterior Segment Image)

Next, the analyzing processor 238 analyzes the anterior segment image 300 with distortion corrected in the step S7 and with the pixel aspect ratio corrected in the step S8, thereby calculating a predetermined anterior segment parameter.

(S10: Display Anterior Segment Image and Analysis Result)

The main controller 211 displays, for example, the anterior segment image 300 with distortion corrected in the step S7 and with the pixel aspect ratio corrected in the step S8, and displays data obtained by the analysis of the step S9, on the display device 241.

In some aspect examples, in the case in which corneal thickness distribution data is obtained in the step S9, the main controller 211 (or the data processor 230) performs registration between the anterior segment image 300 and the corneal thickness distribution data. The main controller 211 then displays the corneal thickness distribution data on the anterior segment image 300 based on the result of the registration.

In some aspect examples, in the case in which a corner angle parameter is calculated in the step S9, the main controller 211 displays the measurement position and the measured value of the corner angle parameter on the anterior segment image 300. Further, the main controller 211 displays the measurement position and the measured value of the corner angle parameter on an enlarged representation of a part of the anterior segment image 300.

(S11: Save Anterior Segment Image and Analysis Result)

The main controller 211 stores one or more anterior segment images of the subject's eye E and the analysis result obtained in the step S9 in, for example, the memory 212 and/or a storage device. The one or more anterior segment images to be stored may include, for example, any of the anterior segment image obtained in the step S1, the anterior segment image with distortion corrected in the step S7, and the anterior segment image with pixel aspect ratio corrected in the step S8. This completes the present operation example (End).

Modification Examples

Figure 15:
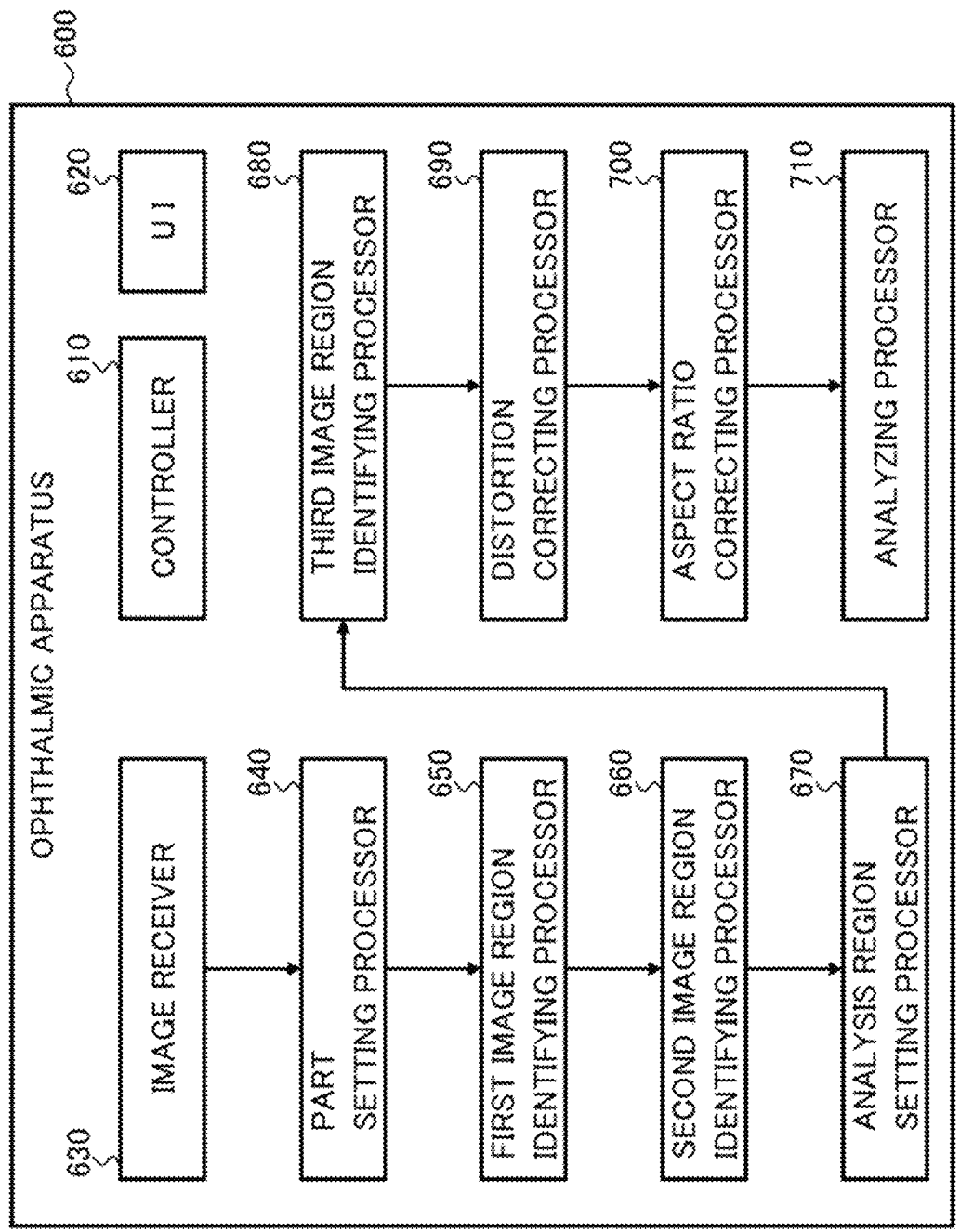
FIG. 15 is a diagram of an example of a configuration of an ophthalmic apparatus according to an aspect example.

While the ophthalmic apparatus 1 described above includes the OCT scanner and the image data constructing unit, an ophthalmic apparatus of some aspect examples may not include any one or both of an OCT scanner and an image data constructing unit. For example, the ophthalmic apparatus 600 shown in FIG. 15 includes neither an OCT scanner nor an image data constructing unit, but includes the image receiver 630 in place of the OCT scanner and the image data constructing unit.

The image receiver 630 has the function of receiving an anterior segment image of a subject's eye from an external source. In some aspect examples, the image receiver 630 may include a communication device for performing data communication with external apparatuses, and may be configured to obtain an anterior segment image of a subject's eye from an external apparatus. In some aspect examples, the image receiver 630 may include a drive device for reading out data stored in a recording medium, and may be configured to obtain an anterior segment image of a subject's eye from a recording medium.

Thus, while the ophthalmic apparatus 1 described above collects data by itself and constructs an OCT image by itself, the ophthalmic apparatus 600 of the present modification example obtains an OCT image from an external source. The ophthalmic apparatus 600 of the present modification example may include, for example, a single computer or two or more computers, and may typically include a personal computer or a server.

Similar to the ophthalmic apparatus 1 described above, the ophthalmic apparatus 600 includes, in addition to the controller 610 and the user interface 620, at least the first image region identifying processor 650 and the second image region identifying processor 660. Further, the ophthalmic apparatus 600 may include the analysis region setting processor 670 and the third image region identifying processor 680. In addition, the ophthalmic apparatus 600 may include one or more of the part setting processor 640, the distortion correcting processor 690, the aspect ratio correcting processor 700, and the analyzing processor 710. Each of these elements may have the same (or similar) configuration and the same (or similar) function as (or to) a corresponding element in the ophthalmic apparatus 1 described above (see, for example, FIG. 5).

An example of the operation of the ophthalmic apparatus 600 will now be described with referring again to FIG. 14. To begin with, the ophthalmic apparatus 600 acquires an anterior segment image of the subject's eye E by the image receiver 630 (S1).

Next, the part setting processor 640 sets the first part 310 for the anterior segment image 300 acquired in the step S1 (S2).

Next, the first image region identifying processor 650 analyzes the first part 310 of the anterior segment image 300 set in the step S2 to identify the first anterior corneal surface image 311 corresponding to the anterior corneal surface of the subject's eye E and the first posterior corneal surface image 315 corresponding to the posterior corneal surface (S3).

Next, based on the first anterior corneal surface image 311 identified in the step S3, the second image region identifying processor 660 identifies the second anterior corneal surface image 331 corresponding to the anterior corneal surface in the entirety of the anterior segment image 300 (more generally, in the second part that includes the first part 310 as a proper subset) (S4). Further, based on the first posterior corneal surface image 315 identified in the step S3, the second image region identifying processor 660 identifies the second posterior corneal surface image 332 corresponding to the posterior corneal surface in the entirety of the anterior segment image 300 (more generally, in the second part that includes the first part 310 as a proper subset) (S4).

Next, the analysis region setting processor 670 sets the anterior surface analysis region 341 that includes the second anterior corneal surface image 331 identified in the step S4 (S5). Further, the analysis region setting processor 670 sets the posterior surface analysis region 342 that includes the second posterior corneal surface image 332 identified in the step S4 (S5).

Next, the third image region identifying processor 680 analyzes the anterior surface analysis region 341 set in the step S5 to identify the third anterior corneal surface image 351 corresponding to the anterior corneal surface (S6). Further, the third image region identifying processor 680 analyzes the posterior surface analysis region 342 set in the step S5 to identify the third posterior corneal surface image 352 corresponding to the posterior corneal surface (S6).

Next, the distortion correcting processor 690 corrects distortion of the anterior segment image 300 based at least on the third anterior corneal surface image 351 obtained in the step S6 (S7).

Next, the aspect ratio correcting processor 700 corrects the pixel aspect ratio of the anterior segment image 300 with distortion corrected in the step S7 (S8).

Next, the analyzing processor 710 analyzes the anterior segment image 300 with distortion corrected in the step S7 and with the pixel aspect ratio corrected in the step S8, thereby calculating a predetermined anterior segment parameter (S9).

Next, the main controller 610 displays, for example, the anterior segment image 300 with distortion corrected in the step S7 and with the pixel aspect ratio corrected in the step S8, and displays data obtained by the analysis of the step S9, on the user interface 620 (S10).

Next, the main controller 610 stores one or more anterior segment images of the subject's eye E and the analysis result obtained in the step S9 in a storage device (S11). This completes the present operation example (End).

<Actions and Effects>

Some features, some actions, and some advantageous effects of some aspect examples of embodiments will now be described.

An ophthalmic apparatus (1; 600) of some aspect examples includes an image acquiring unit (2, 100, 220; 630), a first image region identifying processor (232; 650), and a second image region identifying processor (233; 660). The image acquiring unit is configured to acquire an anterior segment image constructed based on data collected from an anterior segment of a subject's eye by optical coherence tomography (OCT) scanning. The first image region identifying processor is configured to identify a first image region corresponding to a predetermined part of the anterior segment by analyzing a first part of the anterior segment image acquired by the image acquiring unit. The second image region identifying processor is configured to identify a second image region corresponding to the predetermined part based on the first image region identified by the first image region identifying processor. Here, the second image region is located inside a second part that includes the first part as a proper subset.

The ophthalmic apparatus is configured to perform the process of identifying an image of the predetermined part of the anterior segment by analyzing the first part of the anterior segment image, and the process of identifying an image of the same part of the anterior segment from the second part of the anterior segment image, which is larger than the first part, based on the image identified from the first part. This configuration makes it possible, for example, to identify an image of the predetermined part of the anterior segment from the first part in which an artifact does not exist (or in which the influence of an artifact is small), and then to enlarge (expand, extend, increase) this identified image of this part to an image in the second part that is a larger area than the first part. Here, an artifact may exist the second part, or the influence of an artifact may be large in the second part. Therefore, even in the case in which an anterior segment image contains an artifact, segmentation (identification of an image of the predetermined part of the anterior segment) can be performed over a large area of the anterior segment image without being (significantly) affected by the artifact. In this way, the ophthalmic apparatus described above contributes to an improvement in segmentation performed on OCT images of anterior segments.

In some aspect examples, the ophthalmic apparatus (1; 600) may further include an analysis region setting processor (234; 670) and a third image region identifying processor (235; 680). The analysis region setting processor is configured to set an analysis region that includes the second image region identified by the second image region identifying processor. The third image region identifying processor is configured to identify a third image region corresponding to the predetermined part by analyzing the analysis region set by the analysis region setting processor.

With this configuration, an image of the predetermined part can be obtained with a higher degree of accuracy and a higher degree of precision, by analyzing the analysis region including the image of the predetermined part that has been extended from the first part to the second part by the second image region identifying processor. Therefore, it becomes possible to achieve segmentation in a large area of an anterior segment image with a high degree of accuracy and a high degree of precision.

In some aspect examples, the analysis region setting processor may further be configured to set the analysis region by increasing a width of the second image region to a predetermined value.

With this configuration, it becomes possible to apply further analysis to a neighborhood (vicinity, surrounding area) of the image of the predetermined part identified by the second image region identifying processor, thereby further enhancing the accuracy and the precision of segmentation.

In some aspect examples, the third image region identifying processor may further be configured to identify the third image region by applying edge detection to the analysis region set by the analysis region setting processor. In addition, the first image region identifying processor of some aspect examples may further be configured to identify the first image region by applying edge detection to the first part of the anterior segment image.

In some aspect examples in which the first image region identifying processor and the third image region identifying processor both are configured to perform edge detection, a threshold value of a gradient value used in the edge detection performed by the third image region identifying processor may be smaller than a threshold value of a gradient value used in the edge detection performed by the first image region identifying processor.

With such a configuration, for example, while the edge detection for the first part, in which no artifact is contained or in which the influence of an artifact is small, is performed in such a manner as to detect a clear (distinct) edge, the edge detection for the second part, in which an artifact is contained or in which the influence of an artifact is large, is performed in such a manner as to detect an unclear edge due to the influence of the artifact as well as a clear edge. This can achieve an improvement in segmentation as a whole process.

In some aspect examples, the second image region identifying processor may further be configured to identify the second image region by applying curve fitting to the first image region identified by the first image region identifying processor.

With this configuration, it becomes possible to perform the enlargement of the image of the predetermined part of the anterior segment from the first part of the anterior segment image to the second part in an appropriate manner (e.g., easily and/or smoothly).

In some aspect examples, the second image region identifying processor may further be configured to apply, to the first image region, curve fitting designed based on a robust estimation algorithm for removing an outlier. This robust estimation algorithm may include a random sample consensus (RANSAC) algorithm.

With such a configuration, it becomes possible to apply, to the first image region, highly accurate curve fitting with an outlier caused by noise etc. removed, thereby performing acquisition of the second image region that is a good approximation of the shape of the predetermined part of the anterior segment.

In some aspect examples, the OCT scanning may include an A-scan, and a lateral scan perpendicular to the A-scan. Further, the ophthalmic apparatus of some aspect examples may further include a part setting processor (231; 640). The part setting processor is configured to set the first part by setting a part of the anterior segment image that is defined by at least part of an area corresponding to the A-scan and a part of an area corresponding to the lateral scan.

With this configuration, it becomes possible to set the first part of the anterior segment image in such a manner that the first part does not contain an artifact that tends to occur in part in an OCT image. This allows the process of identifying the image of the predetermined part of the anterior segment from the first part of the anterior segment image to be performed in an appropriate manner, and also allows the process of enlarging the image of the predetermined part from the first part to the second part to be performed in an appropriate manner.

In some aspect examples, the lateral scan may include a B-scan. In addition, the part setting processor may further be configured to set the first part by setting a part of the anterior segment image that is defined by the at least part of the area corresponding to the A-scan and an area corresponding to the B-scan with both side regions removed.

With such a configuration, it becomes possible to set the first part of the anterior segment image in such a manner that the first part does not contain an artifact that tends to occur near the side edges (in the side regions) of a B-scan image. Examples of such an artifact include imaginary images (virtual images, inverted images, folded images) and eyelash images. The configuration described here allows the process of identifying the image of the predetermined part of the anterior segment from the first part of the B-scan image to be performed in an appropriate manner, and also allows the process of enlarging the image of the predetermined part from the first part to the second part to be performed in an appropriate manner.

In some aspect examples, the part setting processor may further be configured to detect a feature point by analyzing the anterior segment image, and to set the first part of the anterior segment image based on the feature point detected. In addition, the part setting processor may further be configured to detect the feature point by applying edge detection to an entirety of the anterior segment image. Further, the part setting processor may further be configured to set the first part in such a manner that the first part includes the feature point.

With such a configuration, it becomes possible to set the first part (the position, location, size, area, etc. of the first part) of the anterior segment image on the basis of the feature point (e.g., the corneal apex) regardless of the position (location) of the feature point in the image frame of the anterior segment image. This allows the first part to be set in an appropriate manner on the basis of the features point even in the case in which, for example, the feature point is deviated from the central region of the image frame due to misalignment.

In some aspect examples, the part setting processor may further be configured to apply artifact detection to the anterior segment image. In addition, the part setting processor may further be configured to set the first part in such a manner that the first part does not include an artifact if the artifact is detected from the anterior segment image.

This configuration allows the first part of the anterior segment image to be set in such a manner that the first part does not contain the artifact detected by the artifact detection process. With this, it becomes possible to perform the process of identifying the image of the predetermined part of the anterior segment from the first part of the anterior segment image in an appropriate manner, and also to perform the process of enlarging the image of the predetermined part from the first part to the second part to be performed in an appropriate manner.

The predetermined part of the anterior segment may be a cornea. Described below are aspect examples that may be employed for making an improvement in segmentation in the case in which the predetermined part is the cornea.

In some aspect examples, the first image region identifying processor may further be configured to identify a first anterior corneal surface image corresponding to an anterior surface of the cornea, and a first posterior corneal surface image corresponding to a posterior surface of the cornea, by analyzing the first part of the anterior segment image. In addition, the second image region identifying processor may further be configured to identify a second anterior corneal surface image in the second part corresponding to the anterior surface of the cornea based on the first anterior corneal surface image, and to identify a second posterior corneal surface image in the second part corresponding to the posterior surface of the cornea based on the first posterior corneal surface image.

In some aspect examples, the analysis region setting processor may be configured to set an anterior surface analysis region that includes the second anterior corneal surface image and a posterior surface analysis region that includes the second posterior corneal surface image. Further, the third image region identifying processor may be configured to identify a third anterior corneal surface image corresponding to the anterior surface of the cornea by analyzing the anterior surface analysis region, and to identify a third posterior corneal surface image corresponding to the posterior surface of the cornea by analyzing the posterior surface analysis region.

In some aspect examples, the analysis region setting processor may further be configured to set the anterior surface analysis region by increasing a width of the second anterior corneal surface image to a predetermined value, and to set the posterior surface analysis region by increasing a width of the second posterior corneal surface image to a predetermined value.

In some aspect examples, the third image region identifying processor may further be configured to identify the third anterior corneal surface image by applying edge detection to the anterior surface analysis region, and to identify the third posterior corneal surface image by applying edge detection to the posterior surface analysis region.

In some aspect examples, the first image region identifying processor may further be configured to identify the first anterior corneal surface image and the first posterior corneal surface image by applying edge detection to the first part of the anterior segment image.

In some aspect examples, a threshold value of a gradient value used in the edge detection performed by the third image region identifying processor may be smaller than a threshold value of a gradient value used in the edge detection performed by the first image region identifying processor.

In some aspect examples, the second image region identifying processor may further be configured to identify the second anterior corneal surface image by applying curve fitting to the first anterior corneal surface image, and to identify the second posterior corneal surface image by applying curve fitting to the first posterior corneal surface image.

In some aspect examples, the second image region identifying processor may further be configured to apply curve fitting based on a robust estimation algorithm for removing an outlier, to each of the first anterior corneal surface image and the first posterior corneal surface image. This robust estimation algorithm may include a random sample consensus (RANSAC) algorithm.

In some aspect examples, the OCT scanning may include an A-scan, and a lateral scan perpendicular to the A-scan. In such aspect examples, the part setting processor may set the first part by setting a part of the anterior segment image that is defined by at least part of an area corresponding to the A-scan and a part of an area corresponding to the lateral scan.

In some aspect examples, the lateral scan may include a B-scan. In such aspect examples, the part setting processor may set the first part by setting a part of the anterior segment image that is defined by the at least part of the area corresponding to the A-scan and an area corresponding to the B-scan with both side regions removed.

In some aspect examples, the part setting processor may detect a position corresponding to a corneal apex by analyzing the anterior segment image, and to set the first part of the anterior segment image based on the position corresponding to the corneal apex.

In some aspect examples, the part setting processor may detect the position corresponding to the corneal apex by applying edge detection to an entirety of the anterior segment image.

In some aspect examples, the part setting processor may set the first part in such a manner that the first part includes the position corresponding to the corneal apex.

In some aspect examples, the part setting processor may set the first part in such a manner that the position corresponding to the corneal apex is arranged in a middle position of the lateral scan.

In some aspect examples, the part setting processor may apply artifact detection to the anterior segment image. In the case in which an artifact is detected from the anterior segment image, the part setting processor may set the first part in such a manner that the first part does not include this artifact.

In some aspect examples, the ophthalmic apparatus may further include a first image correcting processor (236; 690) configured to correct a distortion of the anterior segment image based at least on the third anterior corneal surface image.

In some aspect examples, the ophthalmic apparatus may further include a second image correcting processor (237; 700) configured to correct a pixel aspect ratio of the anterior segment image.

In some aspect examples, the ophthalmic apparatus may further include an analyzing processor (238; 710) configured to perform calculation of a predetermined anterior segment parameter by analyzing the anterior segment image.

In some aspect examples, the image acquiring unit may include a data collector (2, 100) configured to collect data by applying the OCT scanning to the anterior segment, and an image constructing processor (220) configured to construct an anterior segment image based on the data collected by the data collector.

In some aspect examples, the image acquiring unit may include a receiver (630) that receives an anterior segment image from outside.

Some aspect examples provide a method of controlling an ophthalmic apparatus. The ophthalmic apparatus to which this control method is applied includes at least a processor. This control method includes the first control step, the second control step, and the third control step.

The first control step is configured to cause the processor to acquire an anterior segment image constructed based on data collected from an anterior segment of a subject's eye by optical coherence tomography (OCT) scanning. The second control step is configured to cause the processor to identify a first image region corresponding to a predetermined part of the anterior segment by analyzing a first part of the anterior segment image. The third control step is configured to cause the processor to identify a second image region corresponding to the predetermined part based on the first image region. Here, the second image region is inside a second part that includes the first part as a proper subset.

Any matters and items of the aspect examples described above may be incorporated with this method of controlling an ophthalmic apparatus.

Some aspect examples provide a program configured to cause a computer (ophthalmic apparatus) to execute the method of controlling an ophthalmic apparatus. Any matters and items of the aspect examples described above may be incorporated with this program.

Some aspect examples provide a computer-readable non-transitory recording medium that retains this program. Any matters and items of the aspect examples described above may be incorporated with this recording medium. This recording medium may be in any form. Examples of this recording medium include a magnetic disk, an optical disk, a magneto-optical disk, a semiconductor memory, and any other kinds of recording media.

The control method, the program, and the recording medium of the aspect examples contribute to an improvement in segmentation performed on OCT images of anterior segments. Further, the control method, the program, and the recording medium of the aspect examples are capable of providing additional actions and additional advantageous effects corresponding to matters and items optionally incorporated.

The aspect examples disclosed herein are merely examples of embodiments of the present invention, and any modifications (e.g., omissions, substitutions, replacements, additions, etc.) can be made within the scope of the gist of the invention.

What is claimed is:

1. An ophthalmic apparatus comprising:
    an image acquiring circuit configured to acquire an anterior segment image constructed based on data collected from an anterior segment of a subject's eye by optical coherence tomography (OCT) scanning;
    a first image region identifying processor configured to identify a first image region corresponding to a predetermined part of the anterior segment by analyzing a first part of the anterior segment image acquired by the image acquiring circuit;
    a second image region identifying processor configured to identify a second image region corresponding to the predetermined part based on the first image region identified by the first image region identifying processor, the second image region being inside a second part that includes the first part as a proper subset;
    an analysis region setting processor configured to set an analysis region that includes the second image region identified by the second image region identifying processor; and
    a third image region identifying processor configured to identify a third image region corresponding to the predetermined part by analyzing the analysis region set by the analysis region setting processor.

2. The ophthalmic apparatus of claim 1, wherein the analysis region setting processor is further configured to set the analysis region by increasing a width of the second image region to a predetermined value.

3. The ophthalmic apparatus of claim 1, wherein the third image region identifying processor is further configured to identify the third image region by applying edge detection to the analysis region set by the analysis region setting processor.

4. The ophthalmic apparatus of claim 3, wherein the first image region identifying processor is further configured to identify the first image region by applying edge detection to the first part of the anterior segment image.

5. The ophthalmic apparatus of claim 4, wherein a threshold value of a gradient value used in the edge detection performed by the third image region identifying processor is smaller than a threshold value of a gradient value used in the edge detection performed by the first image region identifying processor.

6. The ophthalmic apparatus of claim 1, wherein the second image region identifying processor is further configured to identify the second image region by applying curve fitting to the first image region identified by the first image region identifying processor.

7. The ophthalmic apparatus of claim 6, wherein the second image region identifying processor is further configured to apply, to the first image region, curve fitting based on a robust estimation algorithm for removing an outlier.

8. The ophthalmic apparatus of claim 7, wherein the robust estimation algorithm includes a random sample consensus (RANSAC) algorithm.

9. The ophthalmic apparatus of claim 1, wherein the OCT scanning includes an A-scan and a lateral scan perpendicular to the A-scan,
the ophthalmic apparatus further comprising a part setting processor configured to set the first part by setting a part of the anterior segment image that is defined by at least part of an area corresponding to the A-scan and a part of an area corresponding to the lateral scan.

10. The ophthalmic apparatus of claim 9, wherein
the lateral scan includes a B-scan, and
the part setting processor is further configured to set the first part by setting a part of the anterior segment image that is defined by the at least part of the area corresponding to the A-scan and an area corresponding to the B-scan with both side regions removed.

11. The ophthalmic apparatus of claim 9, wherein the part setting processor is further configured to detect a feature point by analyzing the anterior segment image, and to set the first part of the anterior segment image based on the feature point detected.

12. The ophthalmic apparatus of claim 11, wherein the part setting processor is further configured to detect the feature point by applying edge detection to an entirety of the anterior segment image.

13. The ophthalmic apparatus of claim 11, wherein the part setting processor is further configured to set the first part in such a manner that the first part includes the feature point.

14. The ophthalmic apparatus of claim 9, wherein the part setting processor is further configured to apply artifact detection to the anterior segment image, and to set the first part in such a manner that the first part does not include an artifact if the artifact is detected from the anterior segment image.

15. The ophthalmic apparatus of claim 1, wherein
the predetermined part of the anterior segment is a cornea,
the first image region identifying processor is further configured to identify a first anterior corneal surface image corresponding to an anterior surface of the cornea and a first posterior corneal surface image corresponding to a posterior surface of the cornea by analyzing the first part of the anterior segment image, and
the second image region identifying processor is further configured to identify a second anterior corneal surface image in the second part corresponding to the anterior surface based on the first anterior corneal surface image, and to identify a second posterior corneal surface image in the second part corresponding to the posterior surface based on the first posterior corneal surface image.

16. The ophthalmic apparatus of claim 15, further comprising:
an analysis region setting processor configured to set an anterior surface analysis region that includes the second anterior corneal surface image and a posterior surface analysis region that includes the second posterior corneal surface image; and
a third image region identifying processor configured to identify a third anterior corneal surface image corresponding to the anterior surface by analyzing the anterior surface analysis region, and to identify a third posterior corneal surface image corresponding to the posterior surface by analyzing the posterior surface analysis region.

17. The ophthalmic apparatus of claim 16, further comprising a first image correcting processor configured to correct a distortion of the anterior segment image based at least on the third anterior corneal surface image.

18. The ophthalmic apparatus of claim 17, further comprising a second image correcting processor configured to correct a pixel aspect ratio of the anterior segment image.

19. The ophthalmic apparatus of claim 15, wherein the second image region identifying processor is further configured to identify the second anterior corneal surface image by applying curve fitting to the first anterior corneal surface image, and to identify the second posterior corneal surface image by applying curve fitting to the first posterior corneal surface image.

20. The ophthalmic apparatus of claim 15, wherein the OCT scanning includes an A-scan and a lateral scan perpendicular to the A-scan,
the ophthalmic apparatus further comprising a part setting processor configured to set the first part by setting a part of the anterior segment image that is defined by at least part of an area corresponding to the A-scan and a part of an area corresponding to the lateral scan.

21. A method of controlling an ophthalmic apparatus that includes a processor, the method comprising:
causing the processor to acquire an anterior segment image constructed based on data collected from an anterior segment of a subject's eye by optical coherence tomography (OCT) scanning;
causing the processor to identify a first image region corresponding to a predetermined part of the anterior segment by analyzing a first part of the anterior segment image; and
causing the processor to identify a second image region corresponding to the predetermined part based on the first image region, the second image region being inside a second part that includes the first part as a proper subset;
causing the processor to set an analysis region that includes the second image region; and
causing the processor to identify a third image region corresponding to the predetermined part by analyzing the analysis region.

22. A computer-readable non-transitory recording medium storing a program that causes a computer to execute a method comprising:
acquiring an anterior segment image constructed based on data collected from an anterior segment of a subject's eye by optical coherence tomography (OCT) scanning;
identifying a first image region corresponding to a predetermined part of the anterior segment by analyzing a first part of the anterior segment image;
identifying a second image region corresponding to the predetermined part based on the first image region, the second image region being inside a second part that includes the first part as a proper subset;
setting an analysis region that includes the second image region; and
identifying a third image region corresponding to the predetermined part by analyzing the analysis region.

23. An ophthalmic apparatus comprising:
an image acquiring circuit configured to acquire an anterior segment image constructed based on data collected from an anterior segment of a subject's eye by optical coherence tomography (OCT) scanning;

a first image region identifying processor configured to identify a first image region corresponding to a predetermined part of the anterior segment by analyzing a first part of the anterior segment image acquired by the image acquiring circuit; and a second image region identifying processor configured to identify a second image region corresponding to the predetermined part based on the first image region identified by the first image region identifying processor, the second image region being inside a second part that includes the first part as a proper subset, wherein the OCT scanning includes an A-scan and a lateral scan perpendicular to the A-scan, and the ophthalmic apparatus further includes a part setting processor configured to set the first part by setting a part of the anterior segment image that is defined by at least part of an area corresponding to the A-scan and a part of an area corresponding to the lateral scan.

24. A method of controlling an ophthalmic apparatus that includes a processor, the method comprising:

causing the processor to acquire an anterior segment image constructed based on data collected from an anterior segment of a subject's eye by optical coherence tomography (OCT) scanning;

causing the processor to identify a first image region corresponding to a predetermined part of the anterior segment by analyzing a first part of the anterior segment image; and causing the processor to identify a second image region corresponding to the predetermined part based on the first image region, the second image region being inside a second part that includes the first part as a proper subset, wherein the OCT scanning includes an A-scan and a lateral scan perpendicular to the A-scan, and the method of controlling the ophthalmic apparatus further includes causing the processor to set the first part by setting a part of the anterior segment image that is defined by at least part of an area corresponding to the A-scan and a part of an area corresponding to the lateral scan.

25. A computer-readable non-transitory recording medium storing a program that causes a computer to execute a method comprising:

acquiring an anterior segment image constructed based on data collected from an anterior segment of a subject's eye by optical coherence tomography (OCT) scanning;

identifying a first image region corresponding to a predetermined part of the anterior segment by analyzing a first part of the anterior segment image; and identifying a second image region corresponding to the predetermined part based on the first image region, the second image region being inside a second part that includes the first part as a proper subset, wherein the OCT scanning includes an A-scan and a lateral scan perpendicular to the A-scan, and the method further includes setting the first part by setting a part of the anterior segment image that is defined by at least part of an area corresponding to the A-scan and a part of an area corresponding to the lateral scan.

26. An ophthalmic apparatus comprising:

an image acquiring circuit configured to acquire an anterior segment image constructed based on data collected from anterior segment of a subject's eye by optical coherence tomography (OCT) scanning;

a first image region identifying processor configured to identify a first image region corresponding to a predetermined part of the anterior segment by analyzing a first part of the anterior segment image acquired by the image acquiring circuit; and a second image region identifying processor configured to identify a second image region corresponding to the predetermined part based on the first image region identified by the first image region identifying processor, the second image region being inside a second part that includes the first part as a proper subset, wherein the predetermined part of the anterior segment is a cornea, the first image region identifying processor is further configured to identify a first anterior corneal surface image corresponding to an anterior surface of the cornea and a first posterior corneal surface image corresponding to a posterior surface of the cornea by analyzing the first part of the anterior segment image, and the second image region identifying processor is further configured to identify a second anterior corneal surface image in the second part corresponding to the anterior surface based on the first anterior corneal surface image, and to identify a second posterior corneal surface image in the second part corresponding to the posterior surface based on the first posterior corneal surface image.

27. A method of controlling an ophthalmic apparatus that includes a processor, the method comprising:

causing the processor to acquire an anterior segment image constructed based on data collected from an anterior segment of a subject's eye by optical coherence tomography (OCT) scanning;

causing the processor to identify a first image region corresponding to a predetermined part of the anterior segment by analyzing a first part of the anterior segment image; and causing the processor to identify a second image region corresponding to the predetermined part based on the first image region, the second image region being inside a second part that includes the first part as a proper subset, wherein the predetermined part of the anterior segment is a cornea, the method further comprising:

causing the processor to identify a first anterior corneal surface image corresponding to an anterior surface of the cornea and a first posterior corneal surface image corresponding to a posterior surface of the cornea by analyzing the first part of the anterior segment image; and causing the processor to identify a second anterior corneal surface image in the second part corresponding to the anterior surface based on the first anterior corneal surface image, and to identify a second posterior corneal surface image in the second part corresponding to the posterior surface based on the first posterior corneal surface image.

28. A computer-readable non-transitory recording medium storing a program that causes a computer to execute a method comprising:

acquiring an anterior segment image constructed based on data collected from an anterior segment of a subject's eye by optical coherence tomography (OCT) scanning;

identifying a first image region corresponding to a predetermined part of the anterior segment by analyzing a first part of the anterior segment image; and
identifying a second image region corresponding to the predetermined part based on the first image region, the second image region being inside a second part that includes the first part as a proper subset,
wherein
the predetermined part of the anterior segment is a cornea, the method further comprising:
   causing the processor to identify a first anterior corneal surface image corresponding to an anterior surface of the cornea and a first posterior corneal surface image corresponding to a posterior surface of the cornea by analyzing the first part of the anterior segment image; and
   causing the processor to identify a second anterior corneal surface image in the second part corresponding to the anterior surface based on the first anterior corneal surface image, and to identify a second posterior corneal surface image in the second part corresponding to the posterior surface based on the first posterior corneal surface image.

\* \* \* \* \*